US010827945B2

(12) United States Patent
Gillies et al.

(10) Patent No.: US 10,827,945 B2
(45) Date of Patent: Nov. 10, 2020

(54) RADIOLOGICALLY IDENTIFIED TUMOR HABITATS

(71) Applicants: H. LEE MOFFITT CANCER CENTER AND RESEARCH INSTITUTE, INC., Tampa, FL (US); UNIVERSITY OF SOUTH FLORIDA, Tampa, FL (US)

(72) Inventors: Robert J. Gillies, Tampa, FL (US); Robert A. Gatenby, Tampa, FL (US); Natarajan Raghunand, Tampa, FL (US); John Arrington, Tampa, FL (US); Olya Stringfield, Tampa, FL (US); Yoganand Balagurunathan, Tampa, FL (US); Dmitry B. Goldgof, Lutz, FL (US); Lawrence O. Hall, Tampa, FL (US)

(73) Assignees: H. LEE. MOFFITT CANCER CENTER AND RESEARCH INSTITUTE, INC., Tampa, FL (US); UNIVERSITY OF SOUTH FLORIDA, Tampa, FL (US)

( * ) Notice: Subject to any disclaimer, the term of this patent is extended or adjusted under 35 U.S.C. 154(b) by 29 days.

(21) Appl. No.: 15/124,718

(22) PCT Filed: Mar. 10, 2015

(86) PCT No.: PCT/US2015/019594
§ 371 (c)(1),
(2) Date: Sep. 9, 2016

(87) PCT Pub. No.: WO2015/138385
PCT Pub. Date: Sep. 17, 2015

(65) Prior Publication Data
US 2017/0071496 A1 Mar. 16, 2017

Related U.S. Application Data

(60) Provisional application No. 61/950,711, filed on Mar. 10, 2014, provisional application No. 61/955,067, filed on Mar. 18, 2014.

(51) Int. Cl.
*A61B 5/055* (2006.01)
*G01R 33/56* (2006.01)
(Continued)

(52) U.S. Cl.
CPC ............ *A61B 5/055* (2013.01); *A61B 5/0263* (2013.01); *A61B 5/14539* (2013.01);
(Continued)

(58) Field of Classification Search
CPC combination set(s) only.
See application file for complete search history.

(56) References Cited

U.S. PATENT DOCUMENTS 4,922,915 A * 5/1990 Arnold ................... A61B 6/583
378/18
6,909,792 B1 * 6/2005 Carrott .................. G06T 7/0012
382/128

(Continued)

FOREIGN PATENT DOCUMENTS

WO 2010115885 10/2010

OTHER PUBLICATIONS

Abazov VM, et al. Physical review letters. 2011 107(12):121802.
(Continued)

*Primary Examiner* — Tsung Yin Tsai
(74) *Attorney, Agent, or Firm* — Meunier Carlin & Curfman LLC

(57) ABSTRACT

Virtually every cancer patient is imaged with CT, PET or MRI. Importantly, such imaging reveals that tumors are complex and heterogeneous, often containing multiple habi-
(Continued)

tats within them. Disclosed herein are methods for analyzing these images to infer cellular and molecular structure in each of these habitats. The methods can involve spatially superimposing two or more radiological images of the tumor sufficient to define regional habitat variations in two or more ecological dynamics in the tumor, and comparing the habitat variations to one or more controls to predict the severity of the tumor.

14 Claims, 26 Drawing Sheets

(51) Int. Cl.
| | |
|---|---|
| *A61B 5/026* | (2006.01) |
| *A61B 5/145* | (2006.01) |
| *A61B 5/00* | (2006.01) |
| *G01R 33/563* | (2006.01) |

(52) U.S. Cl.
CPC ........ *A61B 5/7264* (2013.01); *G01R 33/5601* (2013.01); *G01R 33/5602* (2013.01); *G01R 33/56341* (2013.01)

(56) References Cited

U.S. PATENT DOCUMENTS

| | | | | |
|---|---|---|---|---|
| 6,956,373 | B1* | 10/2005 | Brown | G01R 33/56 324/309 |
| 7,122,172 | B1* | 10/2006 | Graupner | A61K 51/088 424/9.42 |
| 9,664,760 | B2* | 5/2017 | James | G01R 33/4818 |
| 2002/0061280 | A1* | 5/2002 | Mattrey | A61K 49/225 424/9.52 |
| 2005/0041843 | A1* | 2/2005 | Sawyer | G06T 7/0012 382/128 |
| 2005/0065421 | A1* | 3/2005 | Burckhardt | G06T 7/38 600/407 |
| 2006/0257027 | A1* | 11/2006 | Hero | G06K 9/627 382/190 |
| 2007/0282193 | A1 | 12/2007 | Brown | |
| 2009/0234237 | A1 | 9/2009 | Ross et al. | |
| 2010/0111386 | A1* | 5/2010 | El-Baz | G06T 7/33 382/128 |
| 2011/0288414 | A1 | 11/2011 | Yu et al. | |
| 2012/0316422 | A1* | 12/2012 | Ross | A61B 5/06 600/410 |
| 2013/0004044 | A1* | 1/2013 | Ross | G06T 7/136 382/131 |
| 2014/0270451 | A1* | 9/2014 | Zach | A61B 5/0042 382/131 |
| 2015/0003709 | A1* | 1/2015 | Boernert | A61B 6/032 382/131 |
| 2015/0337034 | A1* | 11/2015 | Schurpf | A61P 21/00 530/387.3 |
| 2016/0109539 | A1* | 4/2016 | Mardor | A61B 5/055 600/420 |
| 2016/0171695 | A1* | 6/2016 | Jacobs | G06T 11/005 382/131 |
| 2016/0314580 | A1* | 10/2016 | Lloyd | G06T 7/0012 |

OTHER PUBLICATIONS

Airley R, et al. Clinical Can Res. 2001 7:928-934.
Asselin MC, et al. (2012). Eur J Cancer 48, 447-455.
Banfield JD and Raferty AE (1993). Biometrics 49, 803-821.
Basanta D, et al. British journal of cancer. 2012 106(1):174-181.
Basu S, et al. 2011 Ieee International Conference on Systems, Man, and Cybernetics (Smc). 2011:1306-1312.
Behrooz A, et al. J Bio Chem. 1997 9:5555-5562.
Benjamin RS, et al. J Clin Oncol. 2007 25(13):1760-4.
Bill-Axelson A, et al. J Natl Cancer Inst. 2008 100(16):1144-1154.
Boado RJ, et al. J Neurochemistry. 2002 80(3):552-554.
Braga-Neto UM, et al. Bioinformatics.20(2):253-258.
Burningham Z, et al. Clin Sarcoma Res. 2012 2(1):14.
Cardenas-Rodriguez J, et al. Magn Reson Imaging. 2012 30(7):1002-9.
Chang CC and Lin CJ (2011). ACM Trans Intell Syst Technol 2, 1-27.
Chicklore S, et al. (2012). Eur J Nucl Med Mol Imaging 40, 133-140.
Clark MC, et al. (1998). IEEE Trans Med Imag 17, 187-201.
Cortes C and Vapnik V (1995). Mach Learn 20, 273-297.
Diehn M, et al. (2008). Proc Natl Acad Sci USA 105, 5213-5218.
Diehn M, et al. Proc Natl Acad Sci U S A. 2008 105(13):5213-5218.
Figueiredo M and Jain A (2002). IEEE Trans Pattern Anal Mach Intell 24, 3:381-3:396.
Fine HA (1994). J Neurooncol 20, 111-120.
Foroutan P K, et al. PLoS One. 2013; vol. 8 Issue 12 Mignion L, et al. Cancer Res.
Galons JP, et al. Neoplasia. 1999 1(2):113-117.
Ganeshan B, et al. (2012). Eur Radiol 22, 796-802.
Gatenby R (2012). Nature 491, S55.
Gatenby R, et al. (2013). Radiology 269, 8-15.
Gatenby RA and Gillies RJ (2008). Nat Rev Cancer 8, 56-61.
Gerlinger M and Swanton C (2010). Br J Cancer 103, 1139-1143.
Gerlinger M, et al. (2012). N Engl J Med 366, 883-892.
Gillies RJ, et al. (2012). Nat Rev Cancer 12, 487-493.
Gillies RJ, et al. Cancer metastasis reviews. 2007 26(2):311-7.
Gillies RJ, et al. IEEE Eng Med Biol Mag. 2004 23(5):57-64.
Gosselaar C, et al. BJU Int. 2008 101(6):685-690.
Greaves M and Maley CC (2012). Nature 481, 306-313.
Gu Y, et al. Pattern Recognition. 2013 46(3):692-702.
Hegde JV, et al. J Magn Reson Imaging. 2013 37(5):1035-1054.
Hoeks CM, et al. Invest Radiol. vol. 48, No. 10, 693-701 2013.
Hua J, et al. EURASIP J Bioinform Syst Biol. 2006 (1).
Huynh AS, et al. PLoS One. 2011 6(5):e20330.
Inda MM, et al. (2010). Genes Dev 24, 1731-1745.
International Search Report and Written Opinion issued in International Application No. PCT/US2015/019594, dated Jun. 9, 2015.
Isebaert S, et al. J Magn Reson Imaging. 2013 37(6):1392-1401.
Jennings D, et al. Neoplasia. 2002 4(3):255-262.
Jordan B, et al. Neoplasia. 2005 7(5):475-85.
Jung SI, et al. Radiology. Nov. 2013;269(2):493-503.
Kaluz S, et al. Biochimica et Biophysica Acta. 2009:162-172.
Kern SE (2012). Cancer Res 72, 6097-6101.
Kim S, et al. J Comp Biology.9(1):127-146.
Klotz L. Pro. J Urol. 2009 182(6):2565-2566.
Koukourakis MI, et al. Clinical Can Res. 2001 7(3399-3403):3399.
Kreahling JM, et al. Mol Cancer Ther. 2012 11(1):174-82.
Kreahling JM, et al. PloS one. 2013 8(3):e57523.
Lambin P, et al. (2012). Eur J Cancer 48, 441-446.
Li BS, et al. 2002 47(3):439-446.
Liu Q, et al. Cancer Chemother Pharmacol. 2012 69(6):1487-98.
Lloyd MC, et al. J Pathol Inform. 2010 1:29.
Marusyk A, et al. (2012). Nat Rev Cancer 12, 323-334.
Mazaheri Y, et al. Radiology. 2008 246(2):480-488.
Mignion L, et a. Cancer Res. Feb. 1, 2014;74(3):686-94.
Meng F, et al. Mol Cancer Ther. 2012 11(3):740-51.
Mirnezami R, et al. (2012). N Engl J Med 266, 489-490.
Morse DL, et al. NMR Biomed. 2007 20(6):602-614.
Nair VS, et al. (2012). Cancer Res 72, 3725-3734.
Norris D. NMR Biomed. 2001 14(2):77-93.
Nowell PC (1976). Science 194, 23-28.
Olive KP, et al. Clin Cancer Res. 2006 12(18):5277-5287.
Otsu N (1979). IEEE Trans Syst Man Cybern 9, 62-66.
Pang KK and Hughes T (2003). J Chin Med Assoc 66, 655-661.
Peng Y, et al. Radiology. 2013 267(3):787-796.
Prastawa M, et al. (2004). Med Image Anal 8, 275-283.
Pucar D, et al. Int J Radiat Oncol Biol Phys. 2007 69(1):62-69.
Rejniak KA, et al. Front Oncol. 2013 3:111.
Schmuecking M, et al. Int J Radiat Biol. 2009 85(9):814-824.
Schuetze SM, et al. The oncologist. 2008 13 Suppl 2:32-40.
Sciarra A, et al. Eur Urol. 2011 59(6):962-977.

(56) References Cited

OTHER PUBLICATIONS

Segal E, et al. Nat Biotechnol. 2007 25(6):675-680.
Sezgin M, et al. Journal of Electronic Imaging. 2004 13(1):146-168.
Shah M, et al. (2011). Med Image Anal 15, 267-282.
Shinagare AB, et al. AJR Am J Roentgenol. 2012 199(6):1193-8.
Shinohara K, et al. J Urol. 1989 142(1):76-82.
Soloway MS, et al. BJU Int. 2008 101(2):165-169.
Soloway MS, et al. European urology. 2010 58(6):831-835.
Somford DM, et al. Invest Radiol. 2013 48(3):152-157.
Sonn GA, et al. J Urol. 2013 189(1):86-91.
Sonoda Y, et al. (2009). Acta Neurochir 151, 1349-1358.
Sottoriva A, et al. (2013). Proc Natl Acad Sci USA 110, 4009-4014.
Stacchiotti S, et al. Radiology. 2009 251(2):447-56.
Stamatakis L, et al. Cancer. 2013 119(18):3359-3366.
Stoyanova R, et al. International Journal of Radiation Oncology Biology Physics. 2011 81(2):S698-S699.
Stoyanova R, et al. Transl Oncol. 2012 5(6):437-447.
Sun JD, et al. Clin Cancer Res. 2012 18(3):758-70.
Tafreshi NK, et al. Cancer Res. 2011 71(3):1050-1059.
Tafreshi NK, et al. Clin Cancer Res. 2012 18(1):207-219.
Tatum JL, et al. Int J Radiat Biol. 2006 82(10):699-757.
Tixier F, et al. (2011). J Nucl Med 52, 369-378.
Turner K, et al. British Journal of Cancer. 2002 1276-1282(86).
van Sluis R, et al. Magn Reson Med. 1999 41(4):743-750.
Vargas HA, et al. Radiology. 2011 259(3):775-784.
Wojtkowiak JW, et al. Cancer Res. 2012 72(16):3938-3947.
Yachida S, et al. (2010). Nature 467, 1114-1117.
Yancovitz M, et al. (2012). PLoS One 7, e29336.
Zhang X, et al. Proc ISMRM. 2012 15:4049.

\* cited by examiner

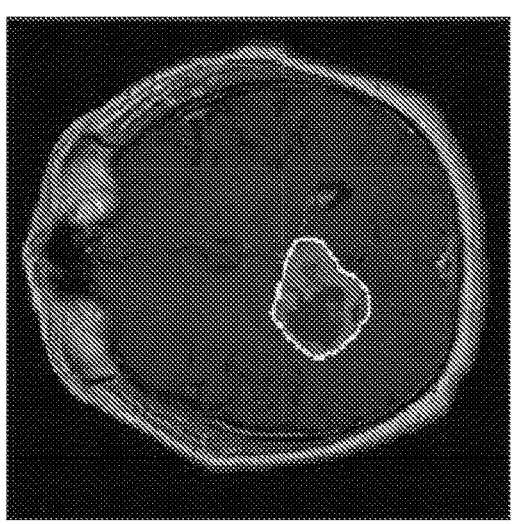
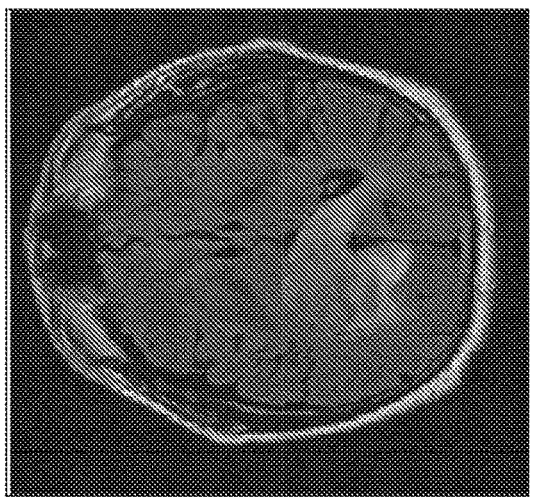
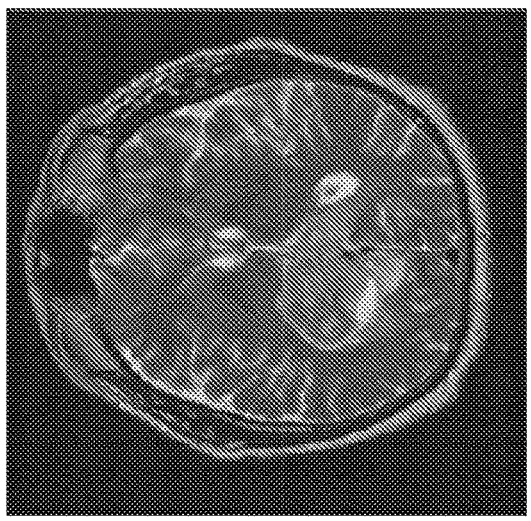
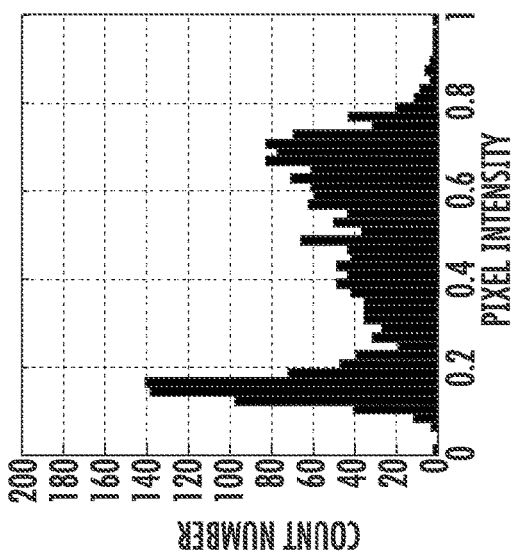
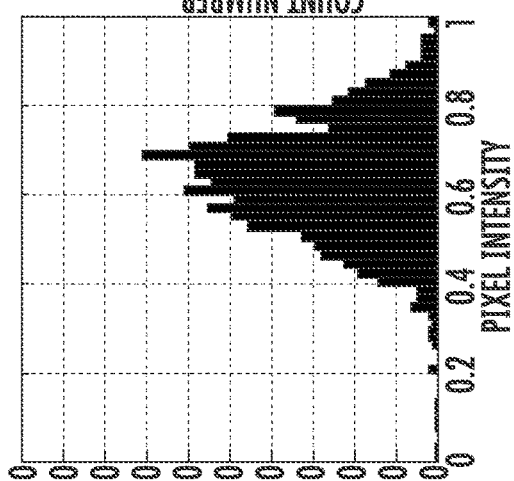
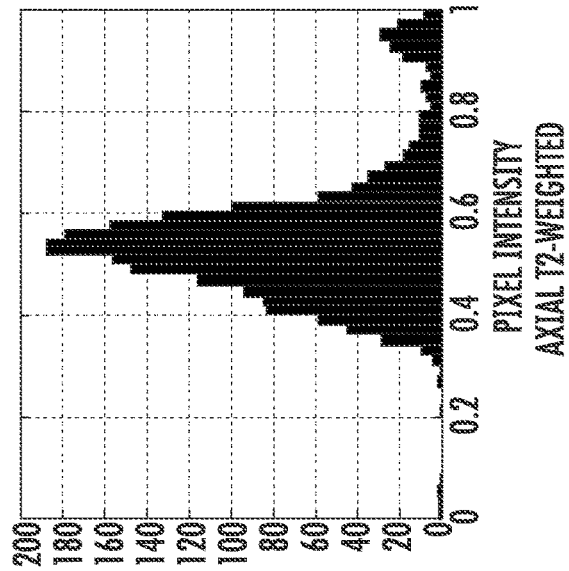
FIG. 1A  FIG. 1B  FIG. 1C

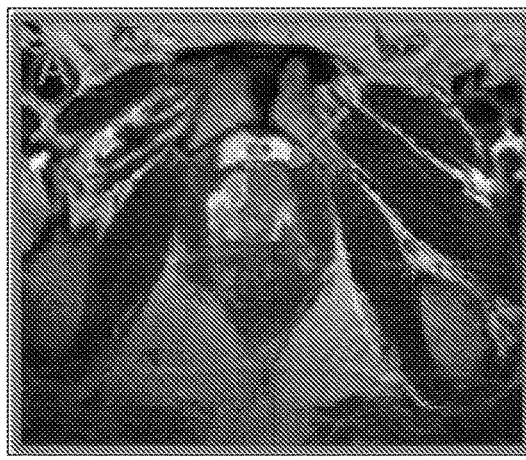
FIG. 21A    FIG. 21B
FIG. 21C    FIG. 21D
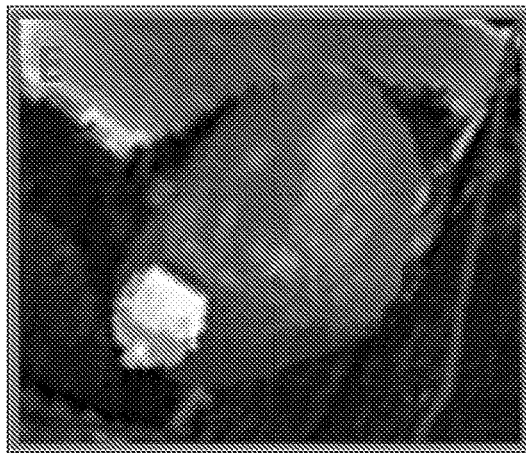
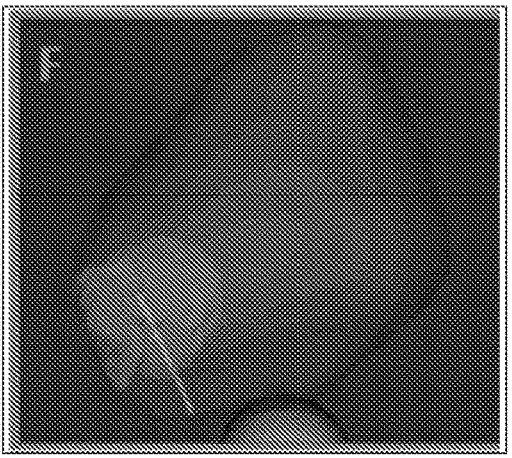
FIG. 21E    FIG. 21F

RADIOLOGICALLY IDENTIFIED TUMOR HABITATS

CROSS-REFERENCE TO RELATED APPLICATIONS

This application claims benefit of U.S. Provisional Application No. 61/950,711, filed Mar. 10, 2014, and U.S. Provisional Application No. Application Ser. No. 61/955,067, filed Mar. 18, 2014, which are hereby incorporated herein by reference in their entirety.

STATEMENT REGARDING FEDERALLY SPONSORED RESEARCH OR DEVELOPMENT

This invention was made with Government Support under Grant No. CA143970, CA143062, CA077575, CA17059, and CA076292 awarded by the National Institutes of Health. The Government has certain rights in the invention.

BACKGROUND

Intratumoral and intertumoral heterogeneities are well recognized at molecular, cellular, and tissue scales [Yancovitz M, et al. (2012). PLoS One 7, e29336; Inda M M, et al. (2010). Genes Dev 24, 1731-1745; Gerlinger M, et al. (2012). N Engl J Med 366, 883-892; Sottoriva A, et al. (2013). Proc Natl Acad Sci USA 110, 4009-4014; Marusyk A, et al. (2012). Nat Rev Cancer 12, 323-334; Yachida S, et al. (2010). Nature 467, 1114-1117]. This is clearly evident in the imaging characteristics of glioblastoma multiforme, which typically include regions of high and low contrast enhancement as well as high and low interstitial edema and cell density. Several recent molecular studies have demonstrated that there is also significant genetic variation among cells in different tumors and even in different regions of the same tumor [Gerlinger M, et al. (2012). N Engl J Med 366, 883-892; Sottoriva A, et al. (2013). Proc Natl Acad Sci USA 110, 4009-4014; Marusyk A, et al. (2012). Nat Rev Cancer 12, 323-334]. In one study, for example, samples from spatially separated sites within kidney tumors found that multiple molecular subtypes were present in all of the examined tumors [Gerlinger M, et al. (2012). N Engl J Med 366, 883-892]. It is clear that this molecular heterogeneity may significantly limit efforts to personalize cancer treatment based on the use of molecular profiling to identify druggable targets [Gerlinger M and Swanton C (2010). Br J Cancer 103, 1139-1143; Mirnezami R, et al. (2012). N Engl J Med 266, 489-490; Kern S E (2012). Cancer Res 72, 1-5]. However, there has, thus far, been little effort to relate the spatial heterogeneity observed in clinical imaging with the genetic heterogeneity found in molecular studies.

SUMMARY

Virtually every cancer patient is imaged with CT, PET, or MRI. Importantly, such imaging reveals that tumors are complex and heterogeneous, often containing multiple "habitats" within them. Methods for analyzing these images to infer cellular and molecular structure in each of these habitats are disclosed.

Disclosed is a radiological method for predicting the severity of a tumor in a subject that involves spatially superimposing two or more radiological images of the tumor sufficient to define regional habitat variations in two or more ecological dynamics in the tumor, and comparing the habitat variations to one or more controls to predict the severity of the tumor. In some cases, the method predicts the survival of the subject based on the severity of the tumor. The methods can also be used to monitor and/or predict a therapy response. The methods can therefore further involve selecting the appropriate treatment for the subject based on the predicted severity of the tumor, e.g., palliative care or adjuvant treatment.

The tumor can be any tumor for which radiological imaging is available. In particular embodiments, the tumor is a glioblastoma multiforme (GBM), prostate cancer, pancreatic cancer, renal cell carcinoma, myxoid tumor, or soft tissue sarcoma.

The methodology described here will produce 3D habitat maps of the analyzed organs which can be used for diagnosis, prognosis, therapy selection, and evaluating response to therapy. This will allow treatment to be individualized for patients based on the tumor habitats. For example, the methods can be used to identify normal and pathological tissue in a patient with GBM and monitor the response of the patient to immunotherapy by detecting immune filtration into the tumor. The methods can be used to diagnose the percentage of sarcomatoid differentiation in a renal cell carcinoma. The methods can also be used to diagnose benign vs. malignant myxoid tumor (e.g., benign intramuscular myxoma vs. malignant myxoid lipsarcoma).

In some embodiments, at least one of the two or more ecological dynamics comprises perfusion (blood flow). In these and other embodiments, at least one of the two or more ecological dynamics comprises interstitial cell density (edema). In these and other embodiments, at least one of the two or more ecological dynamics comprises extracellular pH (pHe). In some embodiments, at least one of the two or more ecological dynamics comprises hypoxia.

Any radiological method suitable to ascertain ecological dynamics of the tumor can be used. For example, the radiological images can be obtained by a magnetic resonance imaging (MRI) sequence. Examples of suitable MRI sequences include longitudinal relaxation time (T1)-weighted images (e.g., pre-contrast or post-contrast; with or without fat suppression), transverse relaxation time (T2)-weighted images, T2*-weighted gradient-echo images, fluid attenuated inversion recovery (FLAIR), Short Tau Inversion Recovery (STIR), perfusion imaging, Arterial Spin Labeling (ASL), diffusion tensor imaging (DTI), and Apparent Diffusion Coefficient of water (ADC) maps.

In some cases, rigid-body and/or elastic image registration can be used to render images from the different MRI sequences superimposable in 3D prior to performing the analysis.

In some embodiments, the regional habitat variations are defined using a fuzzy clustering algorithm analysis of the radiological images. For example, pixels can be classified of into clusters using a variation of the decision tree depicted in FIG. 28. In some embodiments, the regional habitat variations are defined using a thresholding algorithm (e.g. Otsu) analysis of the radiological images.

In some embodiments, the disclosed method separates tumor pixels into distinct clusters representing benign or malignant transformation.

In some embodiments, detection of relatively low heterogeneity in regional habitats is an indication of low severity of the tumor; whereas detection of relatively high heterogeneity in regional habitats is an indication of high severity of the tumor. In some cases, detection of relatively high cell density and relatively high perfusion in the tumor is an indication of low severity of the tumor.

The details of one or more embodiments of the invention are set forth in the accompanying drawings and the description below. Other features, objects, and advantages of the invention will be apparent from the description and drawings, and from the claims.

DESCRIPTION OF DRAWINGS

FIG. 1. An example of an analysis from a single axial plane MRI image from a patient with GBM. For the first row: (A) Boundary outlines the tumor region including enhancement and non-enhancement. (B, C) The corresponding axial plane FLAIR and T2 scans, respectively. The second row illustrates the associated pixel histogram distribution (tumor region).

FIG. 21. MP-MRI findings and directed prostate biopsy of the index lesion. (A) T2w; (B) ADC map (arrow indicating tumor); (C) DCE intensity map (D) Tumor (yellow) and prostate (brown). (E) 3D volumes transferred to Artemis™ for fusion with real-time ultrasound; (F) biopsy needle path.

DETAILED DESCRIPTION

Figure 2:
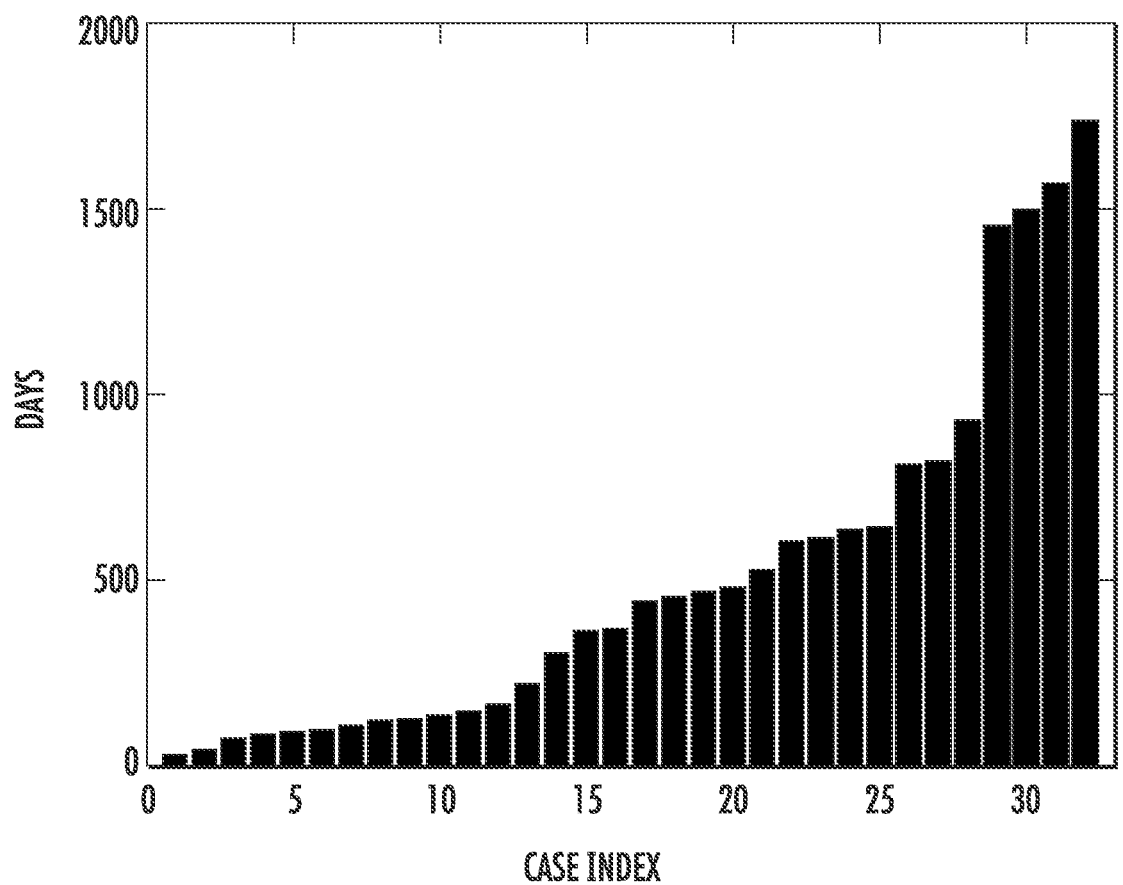
FIG. 2. Survival time distribution demonstrating a broad scale from 16 to 1730 days.

The disclosed methods involve generating radiologically defined "habitats" by spatially superimposing at least two different radiological sequences from the same tumor. The radiological images of the disclosed methods may be scanned images obtained using any suitable imaging techniques. Typical imaging techniques include magnetic resonance imaging (MRI), computerized tomography (CT), positron emission tomography PET, digital subtraction angiography (DSA), single photon emission computed tomography (SPECT), and the like. The exemplary processes described below will be illustrated with reference to a particular type of images, MRI images. Suitable MRI images include T1-weighted (T1), T2-weighted (T2), diffusion-weighted (DWI), perfusion-weighted (FWD, fast fluid-attenuated inversion-recovery (FLAIR), cerebral blood volume (CBV), and echo-planar (EPI) images, apparent diffusion coefficient (ADC) and mean-transit-time (MTT) maps, and the like. However, it is understood that embodiments can be applied for registering other combinations of MRI or other types of images. The images may be represented digitally using intensity histograms or maps where each voxel has a corresponding coordinate and intensity value.

The choice of modalities and mapping procedure can be varied according to the needs of the specific task. In short, as a tool for brain tumor heterogeneity analysis, the design of the spatial habitat concept gave rise to various opportunities for quantitative measurement (e.g., using these habitats to quantitatively observe tumor evolution progress).

The term "subject" refers to any individual who is the target of administration or treatment. The subject can be a vertebrate, for example, a mammal. Thus, the subject can be a human or veterinary patient. The term "patient" refers to a subject under the treatment of a clinician, e.g., physician.

The term "treatment" refers to the medical management of a patient with the intent to cure, ameliorate, stabilize, or prevent a disease, pathological condition, or disorder. This term includes active treatment, that is, treatment directed specifically toward the improvement of a disease, pathological condition, or disorder, and also includes causal treatment, that is, treatment directed toward removal of the cause of the associated disease, pathological condition, or disorder. In addition, this term includes palliative treatment, that is, treatment designed for the relief of symptoms rather than the curing of the disease, pathological condition, or disorder; preventative treatment, that is, treatment directed to minimizing or partially or completely inhibiting the development of the associated disease, pathological condition, or disorder; and supportive treatment, that is, treatment employed to supplement another specific therapy directed toward the improvement of the associated disease, pathological condition, or disorder.

The term "radiomics" refers to the extraction and analysis of large amounts of advanced quantitative MP-MRI features using high throughput methods.

The tumor of the disclosed methods can be any cell in a subject undergoing unregulated growth, invasion, or metastasis. In some aspects, the cancer can be any neoplasm or tumor for which radiotherapy is currently used. Alternatively, the cancer can be a neoplasm or tumor that is not sufficiently sensitive to radiotherapy using standard methods. Thus, the cancer can be a sarcoma, lymphoma, carcinoma, blastoma, or germ cell tumor. A representative but non-limiting list of cancers that the disclosed compositions can be used to treat include lymphoma, B cell lymphoma, T cell lymphoma, mycosis fungoides, Hodgkin's Disease, myeloid leukemia, bladder cancer, brain cancer, nervous system cancer, head and neck cancer, squamous cell carcinoma of head and neck, kidney cancer, lung cancers such as small cell lung cancer and non-small cell lung cancer, neuroblastoma/glioblastoma, ovarian cancer, pancreatic cancer, prostate cancer, skin cancer, liver cancer, melanoma, squamous cell carcinomas of the mouth, throat, larynx, and lung, colon cancer, cervical cancer, cervical carcinoma, breast cancer, epithelial cancer, renal cancer, genitourinary cancer, pulmonary cancer, esophageal carcinoma, head and neck carcinoma, large bowel cancer, hematopoietic cancers; testicular cancer; colon and rectal cancers, prostatic cancer, and pancreatic cancer. In particular embodiments, the tumor is a glioblastoma multiforme (GBM).

A number of embodiments of the invention have been described. Nevertheless, it will be understood that various modifications may be made without departing from the spirit and scope of the invention. Accordingly, other embodiments are within the scope of the following claims.

EXAMPLES

Example 1

Glioblastoma Multiforme

Introduction

Temporal and spatial cellular heterogeneities are typically ascribed to clonal evolution generated by accumulating random mutations in cancer cell populations [Gerlinger M, et al. (2012). N Engl J Med 366, 883-892; Nowell P C (1976). Science 194, 23-28; Greaves M and Maley C C (2012). Nature 481, 306-313]. However, Darwinian dynamics are ultimately governed by the interactions of local environmental selection forces with cell phenotypes (not genotypes) [Gatenby R A and Gillies R J (2008). Nat Rev Cancer 8, 56-61; Gatenby R (2012). Nature 49, 55]. That is, while mutations may occur randomly, proliferation of that clone will proceed only if its corresponding phenotype is more fit than extant populations within the context of the local adaptive landscape. Because of this evolutionary triage of each heritable (i.e., genetic or epigenetic) event, intratumoral evolution is fundamentally linked to the regional variations in microenvironmental selection forces that ultimately determine the fitness of any genotype/phenotype [Gatenby R A and Gillies R J (2008). Nat Rev Cancer 8, 56-61; Gatenby R (2012). Nature 49, 55; Gillies R J, et al. (2012). Nat Rev Cancer 12, 487-493]. The Darwinian dynamics that link genetic changes with environmental conditions will permit the characterization of regional variations in the molecular properties of cancer cells with environmental conditions (such as blood flow, edema, and cell density) that can be determined with clinical imaging [Gatenby R, et al. (2013). Radiology 269, 8-15].

Spatial heterogeneity in tumor characteristics is well recognized in cross-sectional clinical imaging (FIG. 1). Many tumors exhibit significant regional differences in contrast enhancement along with variations in cellular density, water content, fibrosis, and necrosis. In clinical practice, this heterogeneity is typically described in nonquantitative terms. More recently, metrics [Asselin M C, et al. (2012). Eur J Cancer 48, 447-455; Chicklore S, et al. (2012). Eur J Nucl Med Mol Imaging 40, 133-140] of heterogeneity, such as Shannon entropy, have been developed and can be correlated with tumor molecular features [Lambin P, et al. (2012). Eur J Cancer 30, 1234-1248; Nair V S, et al. (2012). Cancer Res 72, 3725-3734; Diehn M, et al. (2008). Proc Natl Acad Sci USA 105, 5213-5218; Segal E, et al. (2007). Nat Biotechnol 25, 675-680] and clinical outcomes [Tixier F, et al. (2011). J Nucl Med 52, 369-378; Pang K K and Hughes T (2003). J Chin Med Assoc 66, 655-661; Ganeshan B, et al. (2012). Eur Radiol 22, 796-802]. However, metrics that assign a single value to heterogeneity tacitly assume that the tumor is "well mixed" and thus does not capture spatial distributions of specific tumor properties.

Disclosed is a spatially explicit approach that identifies and quantifies specific subregions of the tumor based on clinical imaging metrics that can provide information about the underlying evolutionary dynamics. In this approach, tumors will generally possess subregions with variable Darwinian dynamics, including environmental selection forces and phenotypic adaptation to those forces [Gatenby R, et al. (2013). Radiology 269, 8-15]. The approach in this example generates radiologically defined "habitats" by spatially superimposing two different MRI sequences from the same tumor. The goal in this initial work is to examine regional variations in perfusion/extravasation based on T1 post-gadolinium images and interstitial edema/cell density determined by fluid attenuated inversion recovery (FLAIR) and T2 images. Clearly, a full characterization of Darwinian dynamics in intratumor habitats will require more extensive imaging probably from multiple Q6 modalities (i.e., PET, MRI, and CT) or other MRI sequences (particularly apparent diffusion coefficient maps). Nevertheless, in this preliminary study, the following questions were asked: 1) Can GBMs be consistently divided into some small number of specific radiologically defined habitats based on combinations of images sensitive to blood flow and edema? 2) Does the distribution of these regions vary among tumors in different survival groups?

This approach applies a unique ecological/evolutionary perspective that allows clinical imaging characteristics to define regional variations in intratumoral Darwinian dynamics that govern intratumoral molecular heterogeneity. The preliminary studies demonstrate that the distribution of these radiologically defined habitats can be correlated with clinical outcomes.

Materials and Methods

Patient Information

A data set of 32 patients was collected between January and December 2012 from the publicly available TCGA. Although the database contains more than 500 cases, full imaging sets were often not available. Patients were included if they 1) had complete MRI studies that included post-contrast T1-weighted, FLAIR, and T2-weighted sequences and 2) had clinical survival time. Patients were excluded if they had multiple tumors or if the tumor was too small to analyze (<2 cm in diameter). A subset of 66 cases (43 cases with less than 400 days survival and 23 cases with more than 400 days survival) satisfied these two conditions. In the initial analysis, a balanced data set (FIG. 2) was selected that included 16 cases each in group 1 (survival time below 400 days) and group 2 (survival time above 400 days), respectively. The latter 16 were arbitrarily chosen. All of the images had a 200 mm×200 mm field of view and 5-mm slice thickness, with 256×256 or 512×512 acquisition matrices. To ensure uniform resolution of intravariation of each sequence, for each case, three channels were registered by bilinear interpolation. Since the enrolled patients were from multiple institutions, the studies were performed on a wide range of MRI units with some variations in technique.

Image Normalization

To enable consistent evaluations for all cases, the obtained MRI imaging data were processed by standardizing the intensity scales [Shah M, et al. (2011). Med Image Anal 15, 267-282]. Linear normalization on each volume was employed. The voxels of each volume of the tumor region were independently normalized into the scale from 0 to 1. Thus, the normalization captured the local tumor variations of specific patients in the standard range.

Tumor Identification

For consistency, the regions of interest were segmented by manually drawn masks on the post-gadolinium T1-weighted images as shown in FIG. 1. Although automated tumor segmentation meth-Q7 ods have been described [Clark M C, et al. (1998). IEEE Trans Med Imag 17, 187-201; Prastawa M, et al. (2004). Med Image Anal 8, 275-283], they can be unpredictably inaccurate and appeared to offer no advantage over manual segmentation in GBMs where tumor edges are characteristically well defined in T1 post-gadolinium sequences.

Histogram Analysis

For the initial analysis, two-dimensional (2D) histo-Q8 grams (FIGS. 3 and 4) of the cumulative voxel intensities were generated for all tumors. To perform a cohort analysis, the frequencies were rescaled into a range [0,1] using the normalization described above. In the histograms, the y-axis represents the frequency with which a particular MRI sequence intensity (x-axis) was observed.

In addition, 3D histograms (FIG. 5) were used to visually observe variations in tumor heterogeneity. The x- and y-axes consisted of the available pairs of MRI modalities: post-gadolinium T1-weighted and FLAIR, post-gadolinium T1-weighted and T2-weighted, or FLAIR and T2-weighted. A joint histogram that considered the cross-distribution of each modality was used. For instance, considering the pair of post-gadolinium T1-weighted and FLAIR modalities, an aggregated histogram was formed by counting the joint intensity of each voxel $(x_i, x_j)$, where xi was denoted as the T1-weighted intensity signal and $x_j$ was the associated FLAIR intensity signal. The z-axis dimension represented the joint distribution of each voxel. The remaining combinations followed a similar process to obtain the 3D histogram representation.

Survival Time Criterion

The clinical survival time (FIG. 2) was defined as the number of days between the date of the initial pathologic diagnosis and the time to death obtained from the patient demographics in the TCGA database. The MRI imaging data obtained at the initial diagnosis was used, thus the possible influence of the following clinical therapy was not accounted for in this study. Since there was no explicit prior study suggesting the precise survival threshold for different survival groups, the overall statistics in the study were approximately followed [Fine H A (1994). J Neurooncol 20, 111-120], where a reported median value of survival time for malignant brain tumor was 12 to 14 months. In this study, the patient cohort was initially divided into two equal groups: group 1 (survival time<400 days) and group 2 (survival time >400 days), thus the criterion used here differs from that used in another study [Sonoda Y, et al. (2009). Acta Neurochir 151, 1349-1358], which defined long-term survival as more than 3 years (36 months); only 2% to 5% of patients were in this group.

Results

Demographic Data

FIG. 2 and Tables 1-3 summarize the clinical and molecular data. clear separation of the GBM images clear separation of the GBM images survival time <400 days were slightly older (mean age 62) and had more total mutations (n=29) than the group with survival time >400 days (mean age 60, total mutations=25). Only limited information was available on molecular subtype, although recent investigations have shown that multiple subtypes are characteristically observed in each tumor [Sottoriva A, et al. (2013). Proc Natl Acad Sci USA 110, 4009-4014]. The mean tumor diameter and overall volume was slightly greater in group 1, but the difference was not statistically significant. All patients were treated with radiation therapy, chemotherapy, and surgery, although details were not available.

TABLE 1

Data Set of Demographic Information.

|  | Survival < 400 Days (n = 16) | Survival > 400 Days (n = 16) |
|---|---|---|
| Age: Range, median | 47-80, 62 | 18-78, 60 |
| Sex | 8M, 8F | 10M, 6F |
| Histology | Available in n = 9 | Available in n = 11 |
| Classical | 1/9 | 2/11 |
| Mesenchymal | 4/9 | 6/11 |
| Proneural | 3/9 | 2/11 |
| Neural | 1/9 | 1/11 |
| Mutations |  |  |
| CDKN2A | 8 | 11 |
| EGFR | 6 | 8 |
| PTEN | 4 | 3 |
| PDGFRA | 2 | 2 |
| TP53 | 3 | 1 |
| CDK4 | 3 | 0 |
| NF1 | 2 | 1 |
| CDK6 | 1 | 0 |

TABLE 2

Distribution of Gene Mutations in Group 1.

| Tumor ID | CDKN2A | EGFR | PTEN | PDGFRA | TP53 | CDK4 | NF1 | CDK6 | Total |
|---|---|---|---|---|---|---|---|---|---|
| 1 |  |  | X | X | X |  |  |  | 3 |
| 2 |  | X |  |  |  |  |  |  | 1 |
| 3 | X |  |  |  |  |  |  |  | 1 |
| 4 | X | X |  |  |  | X |  |  | 3 |
| 5 | X |  | X | X | X |  |  |  | 4 |
| 6 |  |  |  |  | X |  | X |  | 2 |
| 7 |  |  |  |  |  |  |  |  | 0 |
| 8 |  | X |  |  |  | X |  | X | 2 |
| 9 | X |  |  |  |  |  |  |  | 1 |
| 10 | X |  |  |  |  |  |  |  | 1 |
| 11 | X |  | X |  |  |  | X |  | 3 |
| 12 |  |  |  |  |  |  |  |  | 0 |
| 13 |  | X |  |  |  | X |  |  | 2 |
| 14 |  |  |  |  |  |  |  |  | 0 |
| 15 | X | X |  |  |  |  |  |  | 2 |
| 16 |  | X | X |  |  |  |  |  | 3 |
| Total | 8 | 6 | 4 | 2 | 3 | 3 | 2 | 1 | 29 |

TABLE 3

Distribution of Gene Mutations in Group 2.

| Tumor ID | CDKN2A | EGFR | PTEN | PDGFRA | TP53 | CDK4 | NF1 | CDK6 | Total |
|---|---|---|---|---|---|---|---|---|---|
| 1 | X |  | X |  |  |  |  |  | 2 |
| 2 | X |  |  |  | X |  |  |  | 2 |
| 3 | X | X | X | X |  |  | X |  | 5 |
| 4 |  | X |  |  | X |  |  |  | 2 |

TABLE 3-continued

Distribution of Gene Mutations in Group 2.

| Tumor ID | CDKN2A | EGFR | PTEN | PDGFRA | TP53 | CDK4 | NF1 | CDK6 | Total |
|---|---|---|---|---|---|---|---|---|---|
| 5 | X | X | | | | | | | 2 |
| 6 | | | X | | | | | | 1 |
| 7 | X | X | | | | | | | 2 |
| 8 | | | | | | | | | 0 |
| 9 | | | | | | | | | 0 |
| 10 | X | X | | | | | | | 2 |
| 11 | X | X | | | | | | | 2 |
| 12 | | | | | | | | | 0 |
| 13 | X | X | | | | | | | 2 |
| 14 | X | X | | | | | | | 2 |
| 15 | X | | | | | | | | 1 |
| 16 | X | | | | | | | | 1 |
| Total | 11 | 8 | 3 | 2 | 1 | 0 | 1 | 0 | 25 |

Variations in Blood Flow and Cellular Density

Figure 3:
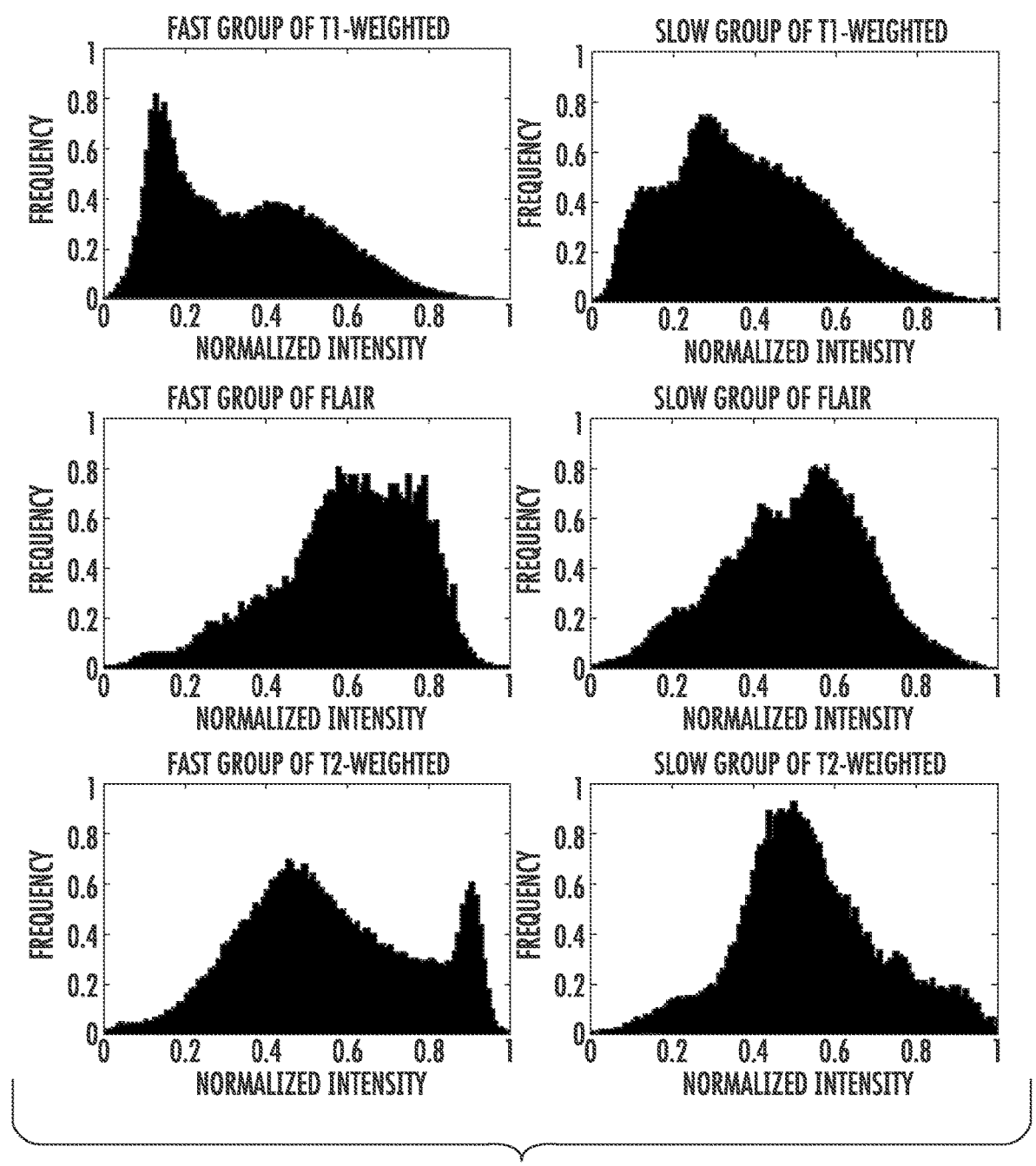
FIG. 3. Two-dimensional histogram distribution. In the responding group, the distribution of normalized values of T1 post-gadolinium, T2-weighted, and FLAIR images was plotted, respectively. Each group was shown as a normalized cumulative histogram.

FIG. 3 demonstrates variation in the normalized values of T1 post-gadolinium, T2-weighted, and FLAIR images in different survival groups. In the T1 post-gadolinium images, there are two populations that are roughly Gaussian distributions around high and low means. This suggests that GBMs are generally divided into regions of high and low contrast enhancement that were viewed as an approximate measure of blood flow. That is, while the dynamics leading to contrast enhancement includes blood flow and vascular integrity (extravasation), it was assumed in the bifurcated classification that the non-enhancing regions have poorer blood flow than the enhancing regions. Group 1 demonstrates a shift in the distribution of these enhancement regions from high to low.

The T2-weighted and FLAIR distributions suggest that group 1 tumors actually contain habitats that are either not present or rare within long-term survival tumors. For both FLAIR and T2-weighted histograms, the tumor volume is dominated by a single population, probably with one other smaller population leading to some asymmetry of the Gaussian distribution. In group 1, tumor set distribution is significantly more heterogeneous with at least three distinct regions.

Initial Spatial Analysis

Figure 4:
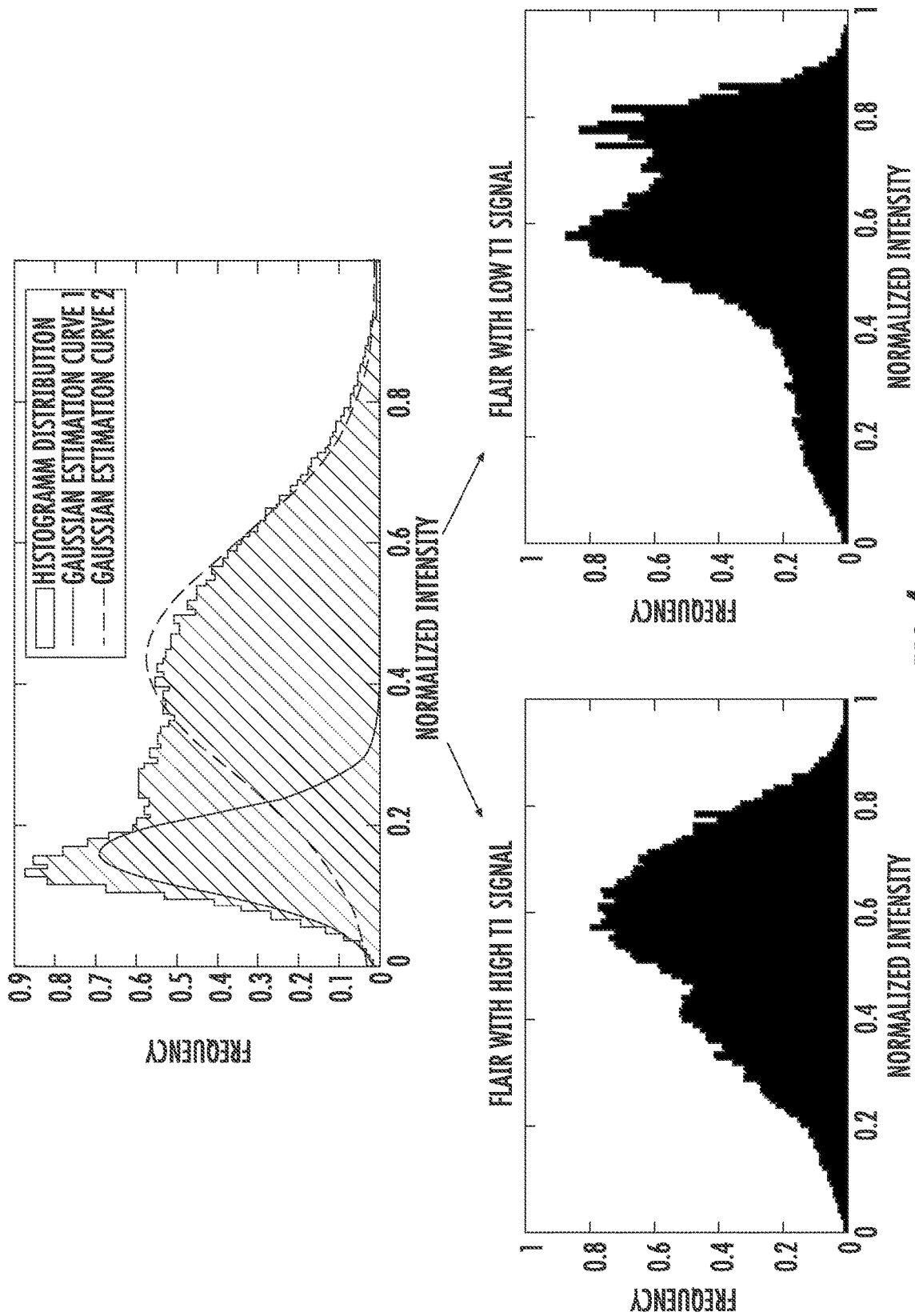
FIG. 4. In the top Figure, the frequency of the normalized values of all T1 post-gadolinium images was plotted. Using a Gaussian mixture mode, the histogram was divided into two Gaussian populations with a separation point of 0.26. The normalized FLAIR signal was then plotted in the high and low groups. The result suggests that GBMs consist of five dominant habitats—two with high blood flow and high and low cell density and three with low blood flow and high, low, and intermediate cell densities.

Since the T1 post-gadolinium images were consistently divided into two regions, this was used as a starting point for combining sequences. All of the tumors were divided spatially into high and low enhancement regions using a normalized intensity of 0.26 as the dividing point. The threshold was found by fitting a Gaussian mixture model [Figueiredo M and Jain A (2002). IEEE Trans Pattern Anal Mach Intell 24, 3:381-3:396; Banfield J D and Raferty A E (1993). Biometrics 49, 803-821] to a cumulative histogram of all T1 post-gadolinium images and finding where two classes intersected. After this spatial division, FLAIR values were projected onto the high and low enhancement groups. As shown in FIG. 4, this resulted in clear separation of the GBM images into five distinct radiologically defined combinations of contrast enhancement and interstitial edema-two with high blood flow and high and low cell density and three with low blood flow and high, low, and intermediate cell densities. In the high enhancement (i.e., high T1 post-gadolinium) regions, there is a region with low FLAIR signal indicating cell density and interstitial edema comparable to normal brain tissue. However, a second habitat with higher FLAIR signal indicates that some tumor regions with high levels of enhancement have lower cell density and higher interstitial edema than normal tissue. Similarly, in the low enhancement regions of the tumor, one subregion shows very high FLAIR signal representing necrosis. However, two additional subregions each with less water and more apparent cellularity are also present. This indicates the presence of viable cell populations that have adapted to local environmental conditions generated by low flow (e.g., hypoxia and acidosis).

Applying Spatial Analysis to Clinical Response

The two groups were analyzed using 3D graphs that plotted the relative frequency of regions with specific combinations of T1 post-gadolinium signal and either FLAIR or T2-weighted signal. As shown in FIG. 4, group 2 tumors typically consist of tumor habitats with high enhancement (i.e., >0.26) and relatively high cell density. Group 1 tumors had increased regions of low enhancement. Interestingly, while these often corresponded to high T2-weighted or FLAIR signal indicating necrosis, regions with low enhancement and relatively high cell density were frequently present.

Statistical Analysis and Clinical Survival Time Group Prediction

Figure 6:
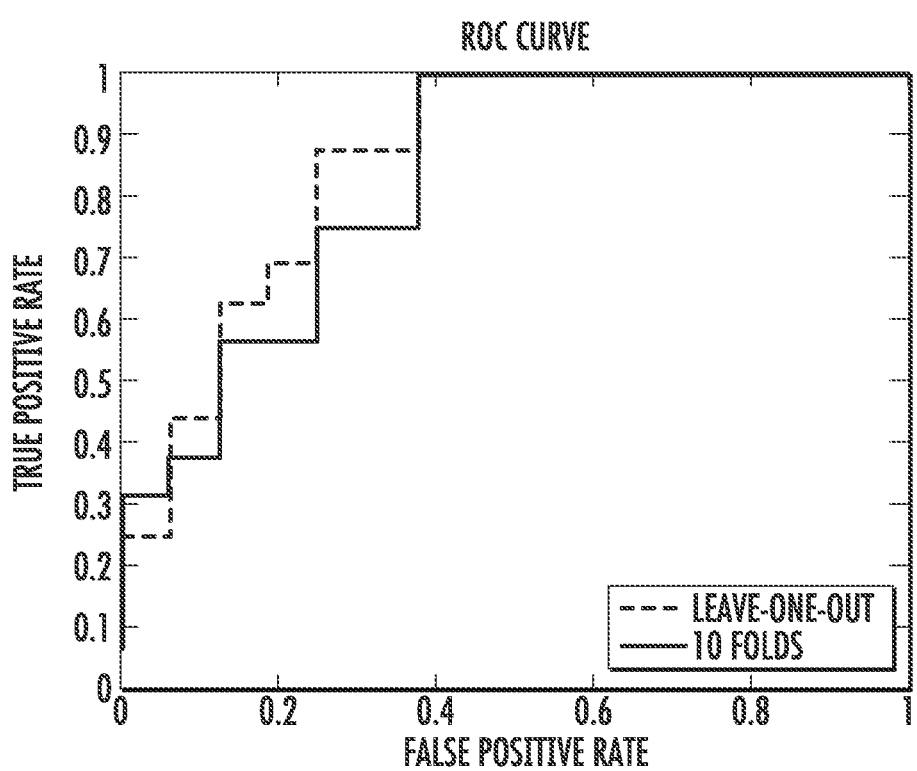
FIG. 6. Prediction results. Both leave-one-out and 10-fold cross-validation schemes were used to validate the prediction performance.

To test the predicative capability, a binary classification scheme (i.e., group 1 and group 2) was formulated. The machine learning classifier, support vector machines [Chang C C and Lin C J (2011). ACM Trans Intell Syst Technol 2, 1-27; Cortes C and Vapnik V (1995). Mach Learn 20, 273-297], was used to classify samples by using a Gaussian kernel function to project features into a high-dimensional space. Both leave-one-out and 10-fold cross-validation schemes were used for performance evaluation. The accuracy (81.25% for leave-one-out), specificity, and sensitivity values were determined with results summarized in Table 4. In addition, ROC curves are shown in FIG. 6, and the associated area under the curve values are also given.

TABLE 4

Prediction Performance.

| Cross-Validation | Accuracy | Specificity | Sensitivity | Area Under the Curve Values |
|---|---|---|---|---|
| Leave-one-out | 81.25% | 77.78% | 85.71% | 0.86 |
| 10-fold | 78.13% | 73.68% | 84.62% | 0.83 |

Spatial Mapping

Figure 7:
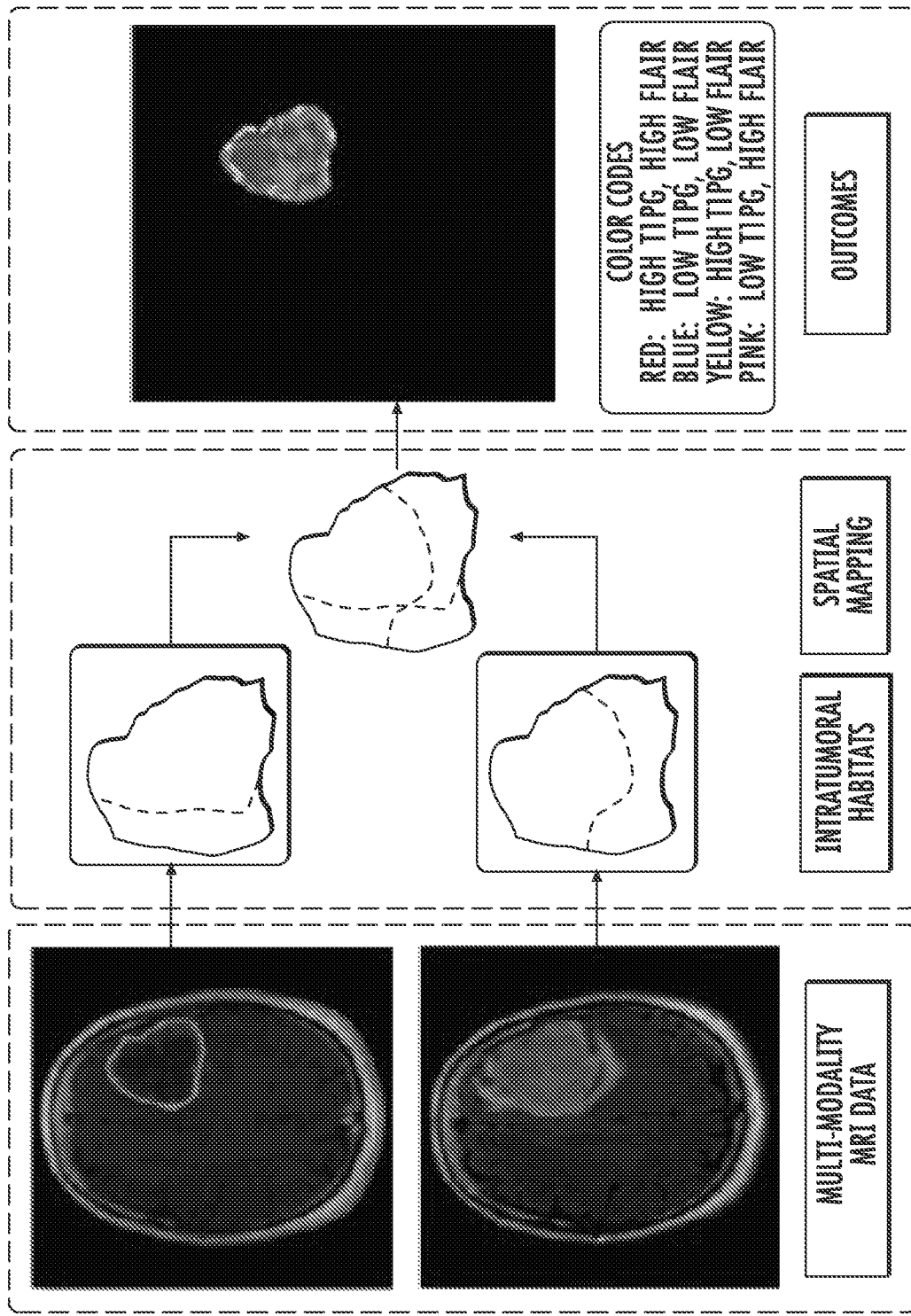
FIG. 7. The block diagram of spatial mapping. For input brain tumor data (e.g., T1-weighted and FLAIR), two intra-tumor habitats were obtained by using the nonparametric Otsu algorithm from each modality separately (as seen from blue and red dashed curves). The following spatial mapping procedure was conducted by an intersection operation. The visual habitats are shown in the last block with color codes.

To examine the spatial clustering of habitats, the combined imaging data sets were divided into four arbitrary habitats—high and low blood flow and high or low cell density. These were then projected back onto the MRI studies. In detail, the nonparametric Otsu segmentation approach [Otsu N (1979). IEEE Trans Syst Man Cybern 9, 62-66] was used for the intratumor segmentation. Given a modality, after setting the number of groups (two groups in this study) to be segmented, the Otsu algorithm iteratively searched for an optimal decision boundary until convergence. As shown in FIG. 7, habitats generally clustered into spatial groups after an intersection operation between two MRI modalities. The choice of modalities and mapping procedure can be varied according to the needs of the specific task. In short, as a tool for brain tumor heterogeneity analysis, the design of the spatial habitat concept gave rise to various opportunities for quantitative measurement (e.g., using these habitats to quantitatively observe tumor evolution progress).

Discussion

Multiple recent studies have demonstrated marked genetic heterogeneity between and within tumors. This is typically ascribed to clonal evolution driven by random mutations. However, genetic mutations simply represent one component ("a mechanism of inheritance") of Darwinian dynamics, which are ultimately governed by phenotypic heterogeneity and variations in environmental selection forces [Gatenby R A and Gillies R J (2008). Nat Rev Cancer 8, 56-61]. While genetic heterogeneity clearly poses a challenge to molecularly based targeted therapy, these variations, rather than a stochastic process governed by random mutations, may represent predictable and reproducible outcomes from identifiable Darwinian dynamics.

In the disclosed model, intratumoral evolution is fundamentally governed by variations in environmental selection forces that are largely dependent on local blood flow. That is, while changes in cancer cells may be the result of random genetic or epigenetic events, clonal expansion of each new genotype is entirely dependent on its fitness within the context of the local environment and the fitness of the competing tumor populations. Thus, the dominant cancer phenotype and genotype within each tumor region is largely determined by their ability to adapt to environmental conditions that are generally governed by blood flow including oxygen, glucose, H+, and serum growth factors. This suggests that only limited numbers of general adaptive strategies are necessary, e.g., evolving the capacity to survive and proliferate in hypoxia. However, the phenotypic expression of those strategies is a much larger set of possibilities and the genetic pathway to those phenotypes is likely very much larger [Gatenby R (2012). Nature 49, 55]. Thus, the genetic variation among cancer cells could look chaotic even when the underlying evolutionary dynamics are fairly straightforward.

This connection between environmental selection forces and phenotypic adaptations/genetic heterogeneity provides a theoretical bridge between radiologic imaging and cellular evolution within tumors. Thus, radiographic manifestation of blood flow and interstitial edema can identify and map distinctive variations in environmental selection forces ("habitats") within each tumor.

To evaluate the potential role of habitat variations in survival, the study group was arbitrarily divided into two groups based on survival time. The disclosed results demonstrate that group 1 and group 2 GBMs have distinctly different patterns of vascularity and cellular density. As shown in FIG. 4, GBMs consistently divide into five MRI-defined combinations of blood flow and cellular density. At present, the underlying evolutionary dynamics cannot be determined unambiguously. Clearly, the expected patterns are high blood flow and high cell density and low blood flow with low cell density. There are three additional regions of apparent mismatch between blood flow and cellular density. In general, it is likely that they represent two possible "ecologies": 1) cellular evolution. This could result in adaptive strategies that permit increased proliferation in regions of poor perfusion or increased utilization of substrate (because of Warburg physiology, for example) that increases glucose uptake and toxic acid production in regions that are well perfused. 2) Temporal variations in regional perfusion. This would result in cycles of normoxia and hypoxia so that the average perfusion results in greater or lesser cellularity than expected based on a single observation.

Figure 5:
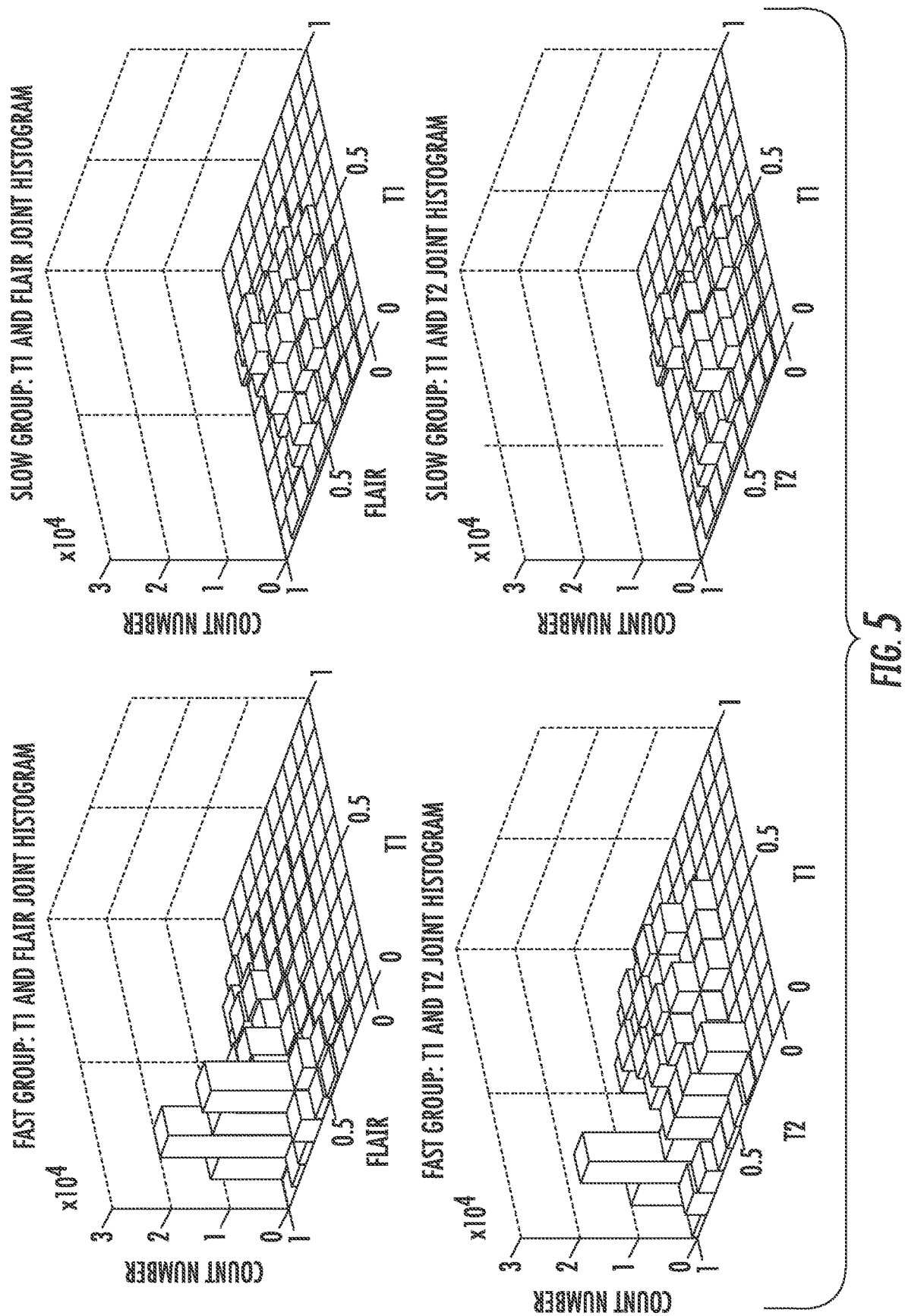
FIG. 5. Three-dimensional histogram distribution shows the relative distribution of combinations of perfusion and cell density in the two groups of GBMs. For each group, we plotted the joint cumulative 3D histogram by summing all cases of 3D histograms of each class. The third dimension is the frequency distribution. Group 2 cases are relatively homogenous with most regions clustering in regions of high perfusion and intermediate cell density. Group 1 cases show greater heterogeneity with Q9 more areas of decreased perfusion with mixed cell density.

As shown in FIG. 5, group 2 tumors were more homogeneous with a dominant habitat in which there is high blood flow and intermediate cell density. Group 1 tumors, however, contain relatively high volumes of low blood flow habitats that may have very low cell density indicating necrosis but often exhibit cell densities comparable to those seen in well-perfused regions.

Multiple factors may be involved including poor perfusion and hypoxia, which may limit the effectiveness of chemotherapy or radiation therapy. Furthermore, hypoxia-adapted cells often exhibit more stem-like behavior with up-regulation of survival pathways that confers resistance to treatments.

As disclosed herein, clinical imaging can be used to gain insight into the evolutionary dynamics within tumors. The disclosed results suggest that combinations of sequences from standard MRI imaging can define spatially and physiologically distinct regions or habitats within the ecology of GBMs and that this may be useful as a patient-specific prognostic biomarker. Ultimately, many other combinations of imaging characteristics including other modalities such as FDG PET should be investigated and may provide greater information regarding intratumoral evolution. Finally, changes in intratumoral habitats during therapy may provide useful information regarding response and the evolution of adaptive strategies.

Example 2

Soft Tissue Sarcomas (STS)

Introduction

Soft tissue sarcomas (STS) are a heterogeneous group of mesenchymal tissue cancers, with over 50 histological sub-types. Regardless of type, the general course of therapy begins with doxorubicin (DOX) followed by resection, if possible. Response rates to DOX are only 25-40% across all histological sub-types and remissions are rarely achieved. Due in part to the rarity and diversity of the many histologic sub-types of STS, there have not been any new front-line therapies approved in over 30 years. A multi-tyrosine kinase inhibitor, pazopanib, was recently approved for relapsed and refractory STS which increases progression free survival by 4 months. Amongst newer agents being developed for STS, TH-302 is showing exceptional promise. TH -302 is an alkylating pro-drug that is activated only in regions of severe hypoxia, and is currently in a phase III trial in combination with DOX in unresectable STS.

Predicting or assessing response in STS is difficult because traditional measures of response based on tumor size change, such as Response Evaluation Criteria in Solid Tumors (RECIST), or those based on relative contrast enhancement (modified Choi) do not correlate well with overall survival (OS) or progression free survival (PFS). A major limitation of these methods is that they do not account for the extreme histological variability within individual tumors prior to and following therapy. In fact, heterogeneous responses are commonly observed among different patients with the same tumor stage and even among different sub-regions within the same tumor. In clinical and pre-clinical STS, distinct intratumoral sub-regions across multiple histological types have been quantitatively delineated by combining T1, contrast-enhanced T1, and T2 STIR MR images. As these are sensitive to tumor physiology, these sub-regions have been classified as "habitats" within STS.

Because TH-302 is active only in hypoxia, and hypoxia should be represented by a specific habitat, "hypoxic" habitats can be used to predict and monitor responses to TH-302 across a variety of histological subtypes of STS. In contrast, response to doxorubicin should be limited to well-perfused portions of the tumor, or "riparian" habitats. Prediction will allow for pre-therapy patient stratification, and monitoring will allow for adaptive therapy trial designs. Furthermore, habitat imaging across different STS types will generate an unprecedented unifying approach to this heterogeneous group of diseases.

Phenotypic habitats can be identified in the clinic with fuzzy clustering algorithmic combinations of T1, T2, T2 STIR, and contrast-enhanced (CE) T1 images. Additional MR observable parameters, such as diffusion, can also be used to define habitats with greater sensitivity and granularity. These studies can develop a minimal MR data set needed to accurately identify relevant habitats in a clinical setting. Images are grossly co-registered to histology and immunohistochemistry (IHC) to identify underlying molecular biochemistry and morphology of individual habitats.

Xenotransplanted tumors can be treated with standard and adaptive dosing schedules of TH-302±doxorubicin. Responses can be quantified as overall survival (OS) and tumor control as defined by the Pediatric Preclinical Testing Program (PPTP). Responses can be compared to pre-therapy habitat images, as well as pre- and post-therapy changes in habitats. Studies can begin with standard dosing, and progress to adaptive dosing informed by changes in habitat volumes.

Effectors can be tested for their ability to increase oxygen consumption in a panel of STS cell lines and STS tumor tissue in vitro. Those with greatest response can be tested in vivo for their ability to acutely enhance tumor hypoxia, and the effects of these agents can be tested for tumor response in combination with TH-302 using STS Xenotransplants.

A clinically viable MR-exam is disclosed that can be used to quantify extent of defined habitats, whether these habitats can be used to predict or monitor therapy response, and whether responses can be improved by manipulating habitats.

Soft Tissue Sarcomas (STS) are a heterogenous group of mesenchymal tumors with >50 histological subtypes. STS are considered rare, with an incidence of 13,170 new cases per year in the U.S. Although they are only 1% of adult malignancies, sarcomas make up 15% of all cancers in patients under the age of 20 [Burningham Z, et al. Clin Sarcoma Res. 2012 2(1):14]. Moffitt is a referral Cancer Center and treats >400 new STS cases every year. Despite the heterogeneity, STS are commonly treated the same, e.g. with doxorubicin (DOX), which delivers a response rate of 25-40%, followed by surgery and radiation, if possible. Median survival can be as long as 10 years in these cases. However, for those that are refractory or recur, median survival is a dismal 18 months. Hence there is a great need for improved therapeutic options. Yet, because of the heterogeneity and rarity of STS, no new front line therapies have been developed to treat STS for decades.

A number of novel chemotherapies for STS are on the horizon. There are currently 13 active phase III interventional drug trials. Most of these are biomarker driven trials using existing agents, yet some are promoting the application of novel chemotherapies. Ifosfamides (e.g. palifosfamide) are DNA-alkylating agents that are increasingly being used in STS in combination with DOX. An exciting advance has come with TH-302, which is a prodrug that has an ifosforamide "warhead" that is released only in regions of profound hypoxia, i.e with pO2<10 mm Hg [Liu Q, et al. Cancer Chemother Pharmacol. 2012 69(6):1487-98; Meng F, et al. Mol Cancer Ther. 2012 11(3):740-51; Sun J D, et al. Clin Cancer Res. 2012 18(3):758-70). TH-302 is currently in 11 active or planned clinical trials, including a phase III in non-resectable STS (Table 5).

TABLE 5

Clinical Trials with TH-302

| | | | |
|---|---|---|---|
| NCT00495144 | Advanced Solid Tumors | C | Phase 1/2 |
| NCT00742963 | +/−Doxorubicin in Advanced Soft Tissue Sarcoma | A | Phase 1/2 |
| NCT01440088 | +/−Doxorubicin in Unresectable or Metastatic Soft Tissue Sarcoma | R | Phase 3 |
| NCT01746979 | +Gemcitabine in Untreated Unresectable Pancreatic Adenocarcinoma | R | Phase 3 |
| NCT01522872 | +/−Bortezomib in Relapsed/Refractory Multiple Myeloma | R | Phase 2 |
| NCT01864538 | A Phase 2 Biomarker - Enriched Study in Advanced Melanoma | N | Phase 2 |
| NCT01381822 | +/−Sunitinib in RCC, GIST and pancreatic Neuroendocrine Tumors | R | Phase 1/2 |
| NCT01497444 | +Sorafenib in unresectable Kidney or Liver Cancer | R | Phase 1/2 |
| NCT01833546 | in Solid Tumors and Pancreatic Cancer (Japan) | R | Phase 1 |
| NCT01149915 | Advanced Leukemias | R | Phase 1 |
| NCT01721941 | +Dox by trans-arterial chemoembolization in HCC | N | Phase 1 |
| NCT01485042 | Pazopanib Plus TH-302 (PATH) advanced solid tumors | R | Phase 1 |

R = recruiting;
N = not yet recruiting;
C = completed;
A = Active no longer recruiting Moffitt Cancer Center is participating in NCT 01440088, which compares TH-302+DOX to DOX alone, with a primary endpoint of OS. DOX (75 mg/m$^2$) is administered on day 1 of a 21-day cycle, for up to 6 cycles. TH-302 (300 mg/m$^2$) is infused on days 1 and 8, and may continue indefinitely on a maintenance basis, as it is well-tolerated, based on phase I data. A secondary endpoint is an objective response measured by RECIST 1.1.

A major limitation in the use of RECIST as an objective endpoint is that many diseases (notably STS) and many therapies do not result in observable changes in tumor size. Hence, specificity can be high, but sensitivity of RECIST is poor to predict survival in STS [Schuetze S M, et al. The oncologist. 2008 13 Suppl 2:32-40; Stacchiotti S, et al. Radiology. 2009 251(2):447-56; Benjamin R S, et al. J Clin Oncol. 2007 25(13):1760-4]. Consequently there is a need to exploit more modern imaging approaches to predict and evaluate response of STS to chemotherapy, whether in a neo-adjuvant or salvage setting. One of the reasons that anatomic size-based methods are deficient is that they treat tumors as homogeneous and well-mixed, which they are not.

Habitat Imaging.

It is well known that malignant tumors are highly heterogeneous in their physical microenvironments, genetics and molecular expression patterns [Gerlinger M, et al. The New England journal of medicine. 2012 366(10):883-92]. Tumors can be described as complete ecosystems, containing cancer cells, stromal cells, vasculature, structural proteins, signaling proteins and physical factors such as pH and oxygen [Gillies R J, et al. Cancer metastasis reviews. 2007 26(2):311-7]. In fact, tumors have been described as "continents", which contain multiple domains with distinct microenvironments. Because these micro-domains, or "habitats", contain unique mixtures of cells, physical and biochemical characteristics, they will have differential responses to therapies and differential evolutionary trajectories [Gillies R J, et al. Nature reviews Cancer. 2012 12(7):487-93]. Knowledge of these habitats can potentially provide patient benefit by stratifying therapeutic choices, and identifying inactive approaches early in the course of therapy.

Magnetic resonance imaging (MRI), which is commonly used to characterize STS, can quantitatively identify distinct habitats within STS, and that these data can be used to monitor and predict therapy response. Such knowledge could have profound impact on the treatment of STS patients in that it will improve decision support systems for choice of therapy and therapy course. Such measures could be made early and often, to assess whether a particular therapeutic treatment is working or not. According to NCCN guidelines, MRI is a preferred imaging modality for STS because of its excellent soft tissue contrast and higher diagnostic potential, compared to computed tomography (CT). Strategies that leverage clinical standard-of-care (SOC) images, with post-processing methods to separate distinct habitats, could be readily implemented into clinical trials and to clinical practice. SOC MRI pulse-sequences commonly include a pre-contrast T1; a T2 STIR; sometimes followed by a diffusion sequence, followed by a contrast-enhanced T1. Each of these provides information relevant to delineation of distinct physiological habitats, as shown in Table 6 [Shinagare A B, et al. AJR Am J Roentgenol. 2012 199(6):1193-8]. Combining these orthogonal pieces of information can better identify distinct habitats; and refining these MR pulse sequences may further improve the ability to identify distinct and therapeutically relevant habitats.

TABLE 6

Information gained from common MR pulse sequences of STS

| Image | Parameter Map |
|---|---|
| T2 FSE | Fast Spin Echo = Borders, edema |
| T2 STIR | Short T1 Inversion Recovery = Fat suppressed |
| (processed) | Subtracting STIR from FSE = Lipid distribution |
| T1 | Baseline |
| T1 CE | Contrast Enhanced = Areas of agent extravasation |
| (processed) | Low CE = Poorly perfused regions |
| GRASE | Gradient and Spin Echo = vascular conspicuity |
| Diffusion | Quantitative Edema (inverse is cellularity) |

Disclosed herein is the interpretation of standard-of-care images using ecology and evolutionary dynamics. Combinations of MR images that contain orthogonal information can be used to identify the distinct habitats that together make up a tumor.

The vasculature of tumors is known to be chaotic: it is tortuous, imbalanced, of low tone, and hyperpermeable. These traits are regionally variable, leading to spatial and temporal variations of oxygen and nutrients. Adaptation of cells to these different perfusion habitats can have profound effects on their molecular expression patterns, their aggressiveness and their therapy responsiveness. Regional differences in oxygenation play an important role in tumor evolution, especially in regions that are intermittently oxygenated. Adaptation to hypoxia involves significant metabolic reprogramming as well as a selection for cells that are apoptosis-deficient [Tatum J L, et al. Int J Radiat Biol. 2006 82(10):699-757].

Disclosed are clinically feasible imaging approaches to quantitative identify habitats in soft tissue sarcomas. Although the current example focuses on "hypoxic" and "riparian" (well-perfused) habitats, other habitats with other distinct cellular behaviors are identifiable by these methods. Hypoxia was chosen because of its relevance to tumor biology, the supposition that hypoxic habitats will be readily identifiable, and the availability of a hypoxia-activated pro-drug, HAP, that is in clinical trials. The HAP approach itself is highly innovative in that it targets a cancer phenotype rather than genotype, which increases its likelihood of managing STS across all histological types.

The disclosed methods also provide a common biomarker platform that will be applicable across all soft tissue sarcomas, regardless of their histology or molecular expression patterns. In a 2×2 clustering system, the same 4 habitats have been observed with differing amounts across 5 types of STS in patients. Hence the habitat imaging approach can lead to the development of a new lexicon that can be used across all STS tumors to provide improved decision support.

The general approach in this example involves 1) acquiring multiple co-registered MR images; 2) using the results from these scans to build up a data cube for each voxel in the image; 3) grouping voxels together that have similar patterns to visualize habitats; 4) in parallel, extracting habitat information from whole mount histology and IHC; and 5) iteratively comparing MR and histology to generate a more precise descriptions of the habitats. This general approach can be applied to human-in-mice xenotransplant sarcoma tumors, and to cultured sarcoma cells and xenografts. A pre-clinical trial can also be conducted, wherein the image-defined hypoxic habitat is used to predict and monitor the response to doxorubicin and the hypoxia activated pro-drug, TH-302. This can be used to develop biomarker-driven trials going forward.

Results
Differentially Define MRI-Visible Habitats in STS

Figure 8B:
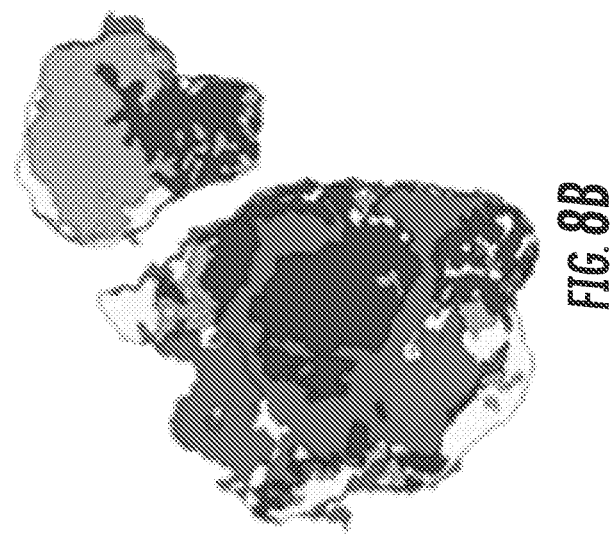
FIG. 8. Osteosarcoma Xenotransplant. (A) H&E of whole mount. (B) individual cells were segmented and clustered according to Haralick textures of nuclei, nuclear size and eosin density features to identify sub-regions with similar morphotypes.
Figure 8A:
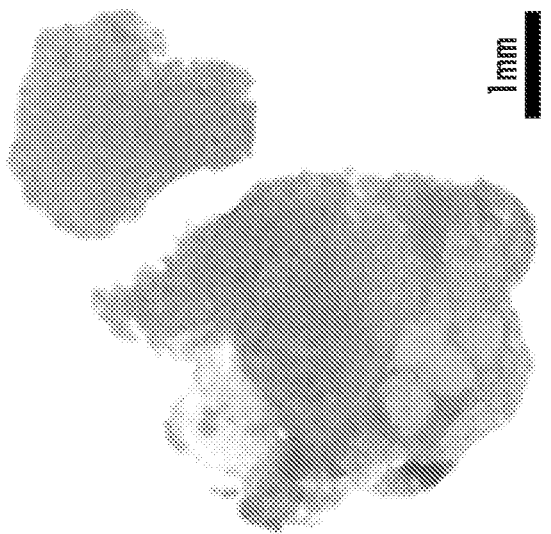
Figure 9:
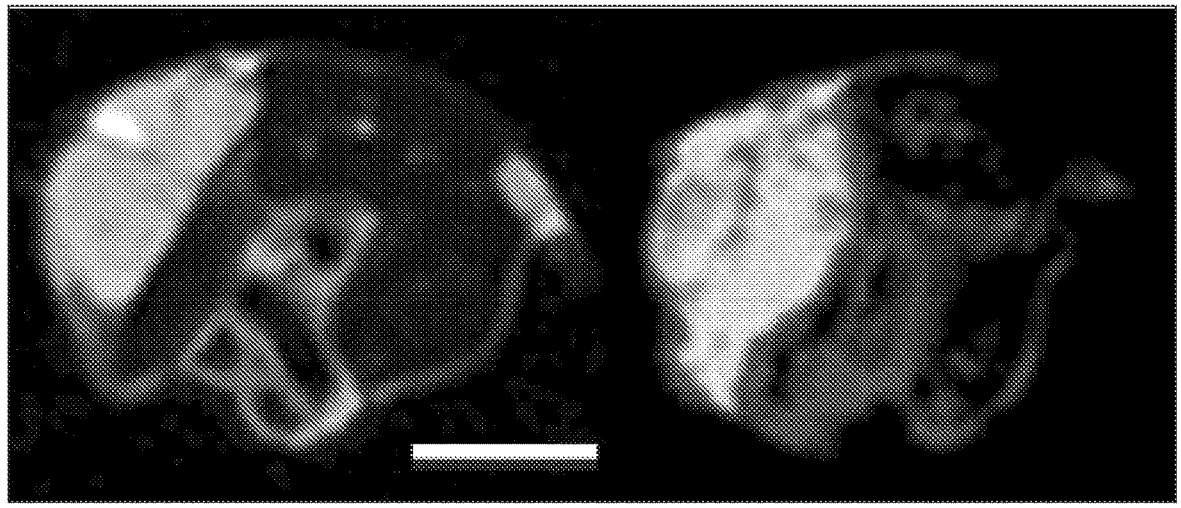
FIG. 9. FSE (L) and ADC map (R) of osteosarcoma xenotransplants in SCID mouse. Bar=8 mm.

Whole-mount histology of the osteosarcoma xenotransplant is shown in FIG. 8A, and these H&E data were analyzed using quantitative histopathology to identify clusters of cells with similar combinations of morphological features, shown in FIG. 8B. This was achieved using Definiens Developer XD and Tissue Studio platforms to automatically identify all nuclei (up to 50,000 per field), and cell boundaries, as described above and in [Lloyd M C, et al. J Pathol Inform. 2010 1:29]. A report is then generated that extracts 32 features from each cell. In this example, cells were clustered according to their nuclear area, Haralick texture of nucleus and intensity of eosin staining into five sub-regions with similar morphotypes. There are two important consideration from these analyses: (1) While some of these clusters are very small, there are at least 3 clusters that are >2 mm and thus visible by MRI (cf. FIG. 9). Thus, 1 mm, was the target precision for registering MR with histology. Further, (2) IHC images can be used to identify the molecular phenotypes within these habitats. FIG. 9 shows a representative set of spin echo T2 and diffusion images from an osteosarcoma xenotransplant. In the T2 image, note that the tumors exhibit a significant amount of regional heterogeneity. The diffusion maps were calculated to display the Apparent Diffusion Coefficient, with a large dynamic range. High diffusion (>3 $u^2$ $sec^{-1}$=red) is associated with edema, which is commonly found in necrotic volumes. Low diffusion (~1.2 $u^2$ $sec^{-1}$=dark blue) is associated with high cell density. Notably, volumes with high cell density will have a higher oxygen consumption rate and be more prone to hypoxia. Thus, we propose that areas of low diffusion that are adjacent to areas of high diffusion are hypoxic. Such volumes can be visualized by plotting and analyzing ADC gradient maps.

Figures 10A, 10B:
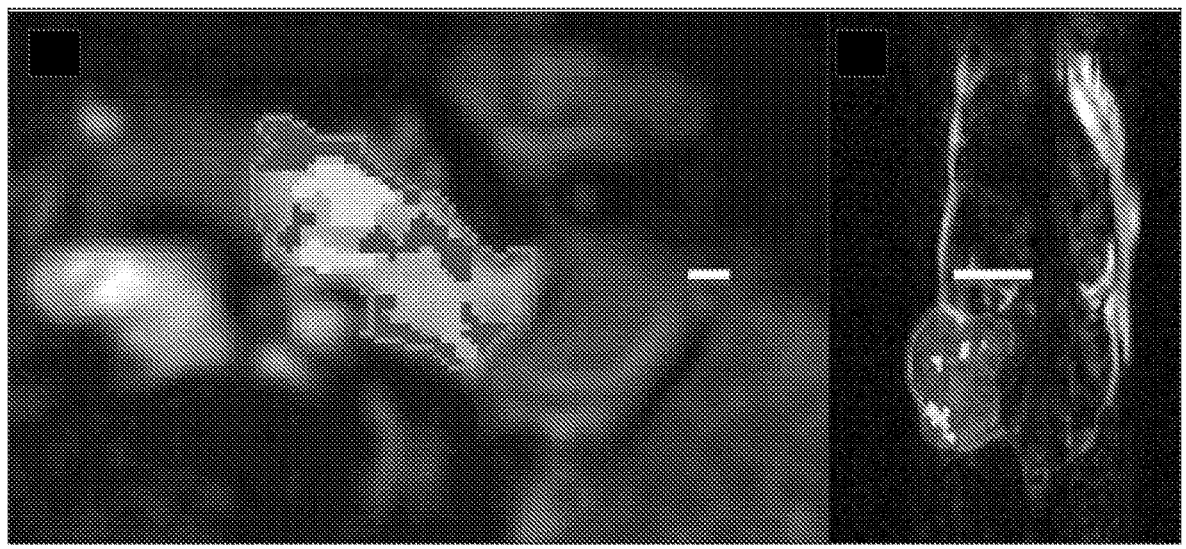
FIG. 10. MR imaging of "Habitats" in PDAC (bars=1 cm). Contrast-Enhanced T1w and ADC maps were obtained in both (A) clinical and (B) preclinical (MiaPaCa xenograft) subjects. The lowest quartile of T1 weighted maps was used as a mask to mark volumes with the lowest blood flow/perfusion. Within this, the areas within the (A) highest quartile of ADC (lowest cell density) were masked in green to mark "NECROSIS"; and (B) lowest quartile of ADC (highest cell density) were masked in purple to mark "HYPDXIA".

To further examine possibilities of imaging hypoxia, imaging can be done with diffusion and dynamic contrast enhanced (DCE) MRI. The rationale for this approach is shown in Table 7. Volumes with lowest signal on contrast enhanced (CE) T1 are in some embodiments poorly perfused. Within these volumes, low cell density would be found in necrotic areas, whereas, in contrast, high cell densities would have highest oxygen consumption and thus be more prone to hypoxia. Additionally, barring biochemical chemo-resistance mechanisms, those volumes that are well perfused with high cell density areas would experience higher drug concentrations and thus be most responsive to, e.g. doxorubicin, chemotherapy. Diffusion (DW) MRI is a quantitative measure of edema and necrosis [Jordan B, et al. Neoplasia. 2005 7(5):475-85; Norris D. NMR Biomed. 2001 14(2):77-93], and necrotic volumes are commonly observed adjacent to hypoxia. FIG. 10 shows T2 images of (A) a pancreatic cancer patient and (B) an orthotopic MiaPaCa-2 pancreatic onto which were identified those pixels that had the lowest quartile in Contrast Enhanced T1 images and either the highest quartile ADC values (green=necrosis) or the lowest quartile (purple="hypoxia"). These 3D MR images can be compared to 2D histology, or immunohistochemistry of biological and tracer hypoxia markers.

TABLE 7

| | MRI visible habitats | | |
|---|---|---|---|
| | | Diffusion (ADC) | |
| | | Lowest ¼ (high cell density) | Highest ¼ (edema) |
| CE T1 | Lowest Quartile (poorly perfused) | HYPOXIC (purple) | NECROTIC (green) |
| | Highest Quartile (well perfused) | RIPARIAN (grey) | Not observed |

Figure 11:
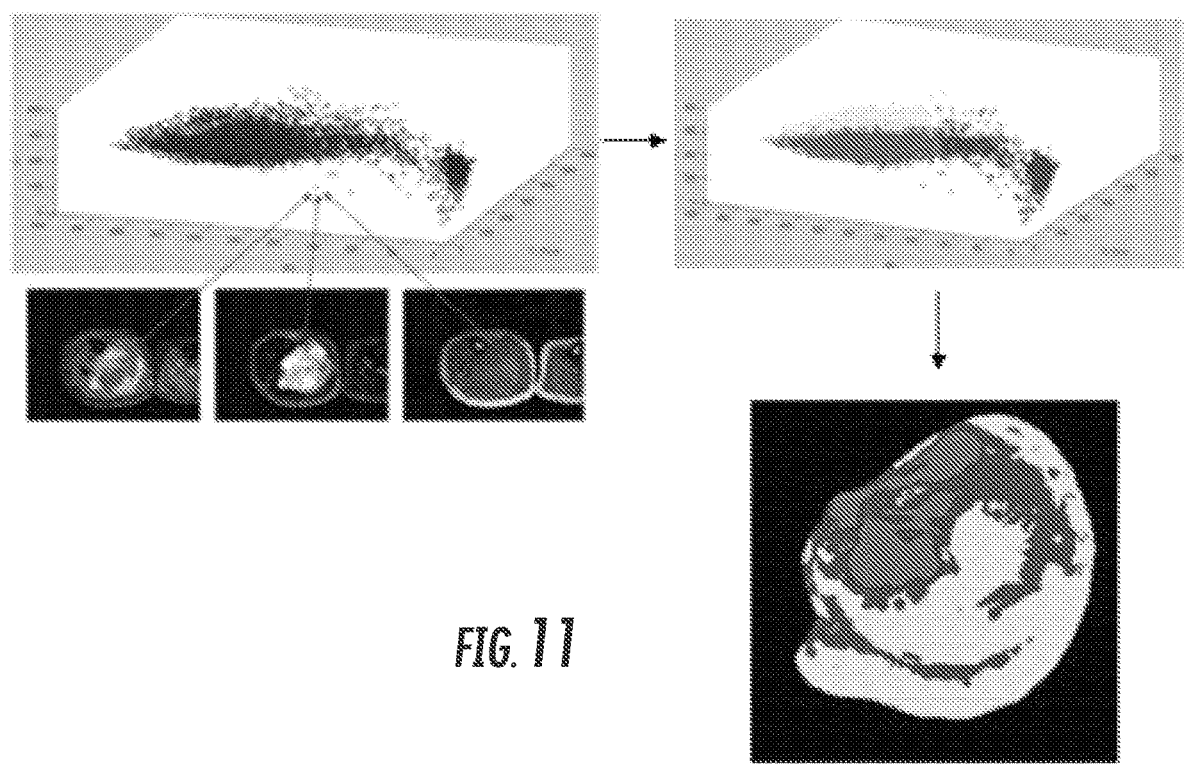
FIG. 11. Clinical STS Images: Each pixel value in the tumor is plotted on axes representing each sequence (T1, STIR/T2, post contrast). Using Fuzzy c-means clustering technique, data points are clustered. Each cluster is assigned a color and then presented in 2D space on the tumor mask as a color segmentation map.

In a pilot study, clinical T1-weighted pre-contrast, T1-post contrast and T2-STIR were analyzed, where the inversion delay Ti is set to null out the signal from fat, and the results are shown in FIG. 11. As shown in FIG. 11, the orthogonal data can be combined using Fuzzy C-means and Otsu segmentation clustering to identify spatially explicit habitats in STS. This has been performed in 5 different histological subtypes, all of whom show the same collection of habitats, albeit in different proportions.

Relate Habitats to Therapy Response

Figure 12:
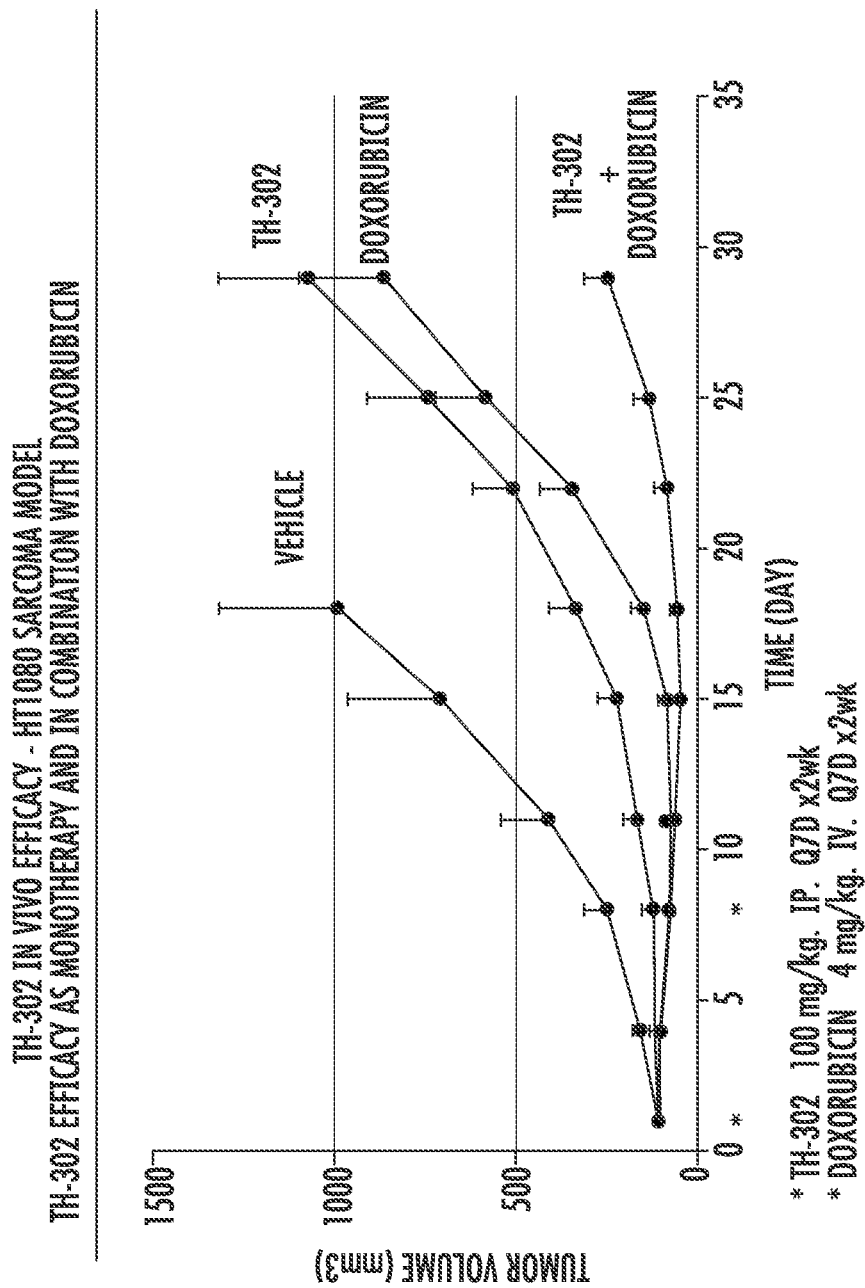
FIG. 12. Response of HT1080 Sarcoma to TH-302+DOX with standard dosing.

FIG. 12 shows the response of HT1080 Sarcoma tumors in SCID mice following treatment with vehicle, TH-302, doxorubicin and (TH-302+doxorubicin). As shown, these two agents combine for maximum cell kill. Notably, this synergy is only observed if TH-302 is given prior to doxorubicin. This is interpreted as evidence that doxorubicin will exert its effects to the cells closest to patent vasculature and that TH-302 exerts its effects on cells in poorly perfused regions (see Table 7). If doxorubicin is effective in killing cells adjacent to the vasculature, it will result in expanding the effective diffusion distance of 02 due to lack of consumption by intervening cells, thus expanding the well-oxygenated volume and reducing efficacy of TH-302.

In a parallel study, DCE-MRI and Diffusion MRI were investigated as response biomarkers to TH-302 in flank implanted MiaPaCa2 pancreatic adenocarcinoma (PDAC) models. These studied showed a strong correlation between initial drop in $K_{trans}$ and tumor control, with no differences in ADC at any time point [Cardenas-Rodriguez J, et al. Magn Reson Imaging. 2012 30(7):1002-9]. In a follow-on study, orthotopically implanted Hs766t, MiaPaCa2 and Su.86.86 PDAC cells were used, which have differential sensitivities to TH-302 as monotherapy. These studies showed decreases in Ktrans in the responsive Hs766t and MiaPaCa2, but not the resistant Su.86.86 in response to TH-302. Notably, no changes in the mean ADC were observed, and these studies underscore the need for improved imaging response biomarkers for TH-302 therapy.

Combined MRI and histology image analyses were used to examine effects of dasatinib+Tcn in a Ewings sarcoma model; and the response to a novel Wee-1 checkpoint inhibitor, MK1775, alone and in combination with gemcitabine in osteosarcoma xenotransplants [Kreahling J M, et al. Mol Cancer Ther. 2012 11(1):174-82; Kreahling J M, et al. PloS one. 2013 8(3):e57523]. In the Ewing's model, the pre-therapy spin-echo T2 and post-therapy response of ADC were compared to tumor volume changes. These analyses showed that the change in ADC within 24 hr following therapy was a powerful predictor of eventual tumor volume change following therapy. Notably, as mentioned above, TH-302 does not appear to invoke a change in ADC to presage response.

Figure 13:
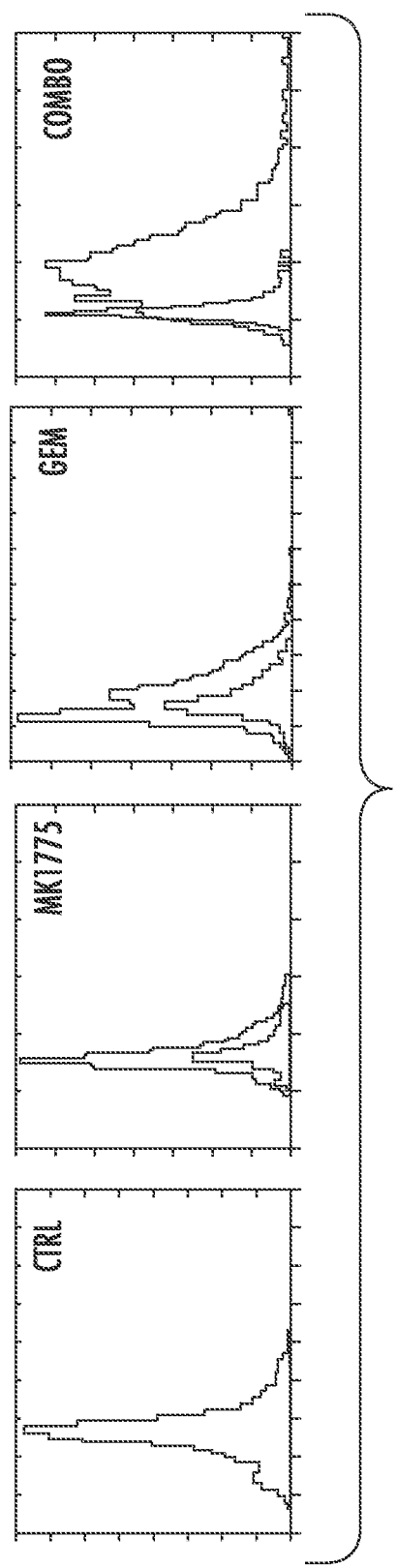
FIG. 13. Pixel-by-pixel histograms demonstrating the ADC distribution pre- (blue) and post-treatment on day 2 (red) for select animals from all four treatment groups and corresponding quantitative analysis of percent change (average) in relative ADC.

In the osteosarcoma xenotransplant models, the change in ADC was measured following treatment with gemcitabine and the wee-1 inhibitor MK-1775, alone and in combination. As shown in FIG. 13, the ADC histograms shifted to the right within 48 hr following gemcitabine and combination therapy groups, which had a robust anti-tumor response; but not control or MK-1775 mono-therapy groups, which were non-responsive. The change in ADC was highly correlated with tumor growth rate response. Also, the shapes of the histograms changed with response, going from Gaussian to a log-normal distributions, with increased skewness.

Figure 14A:
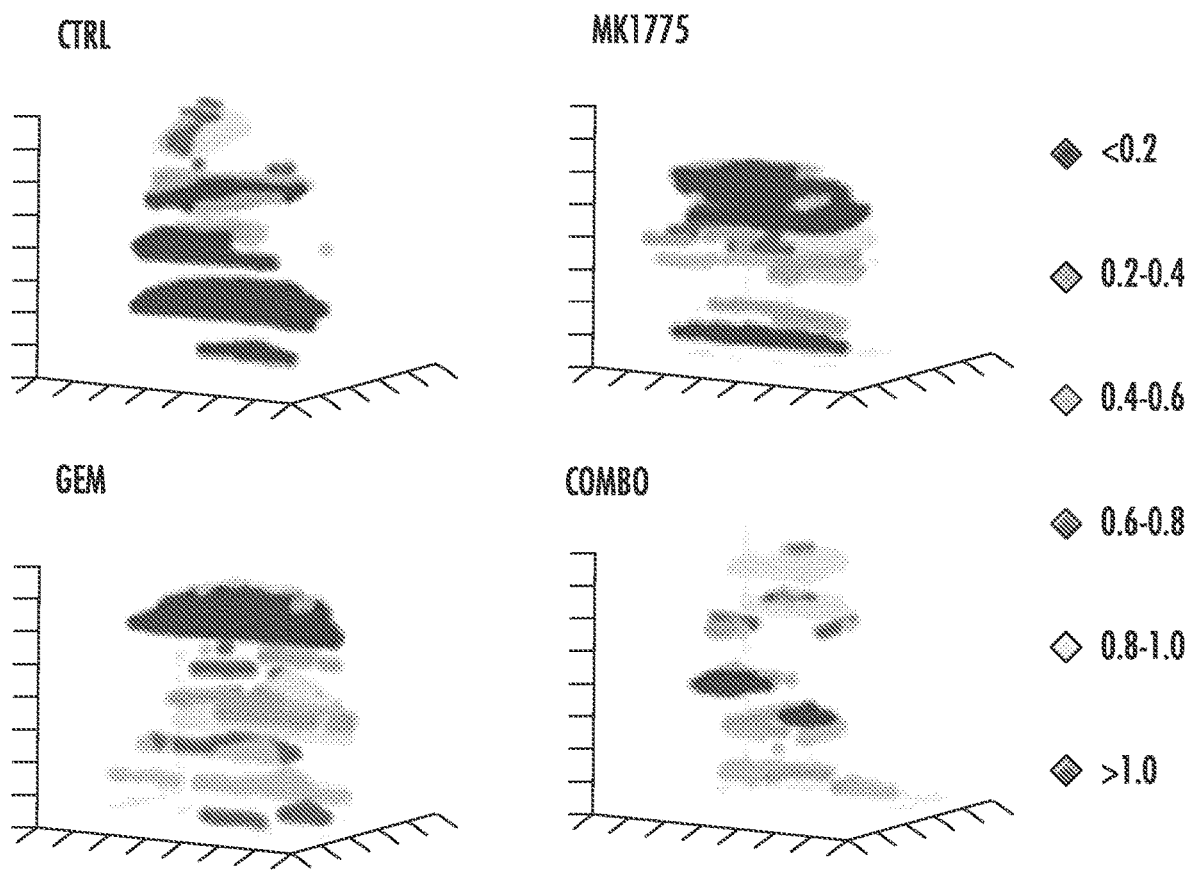
FIG. 14. (A) ADC-entropy plots as obtained by texture-based analysis of post-treatment ADC-maps herein demonstrating the evident differences in ADC values and distribution within the perimeters of the tumor (see color bar). (B) Corresponding change in average entropy values from pre-treatment for all four groups displaying statistically larger variations in ADC values for the Gem group compared to both controls ($p=0.022$) and MK1775 ($p=0.023$).
Figure 14B:
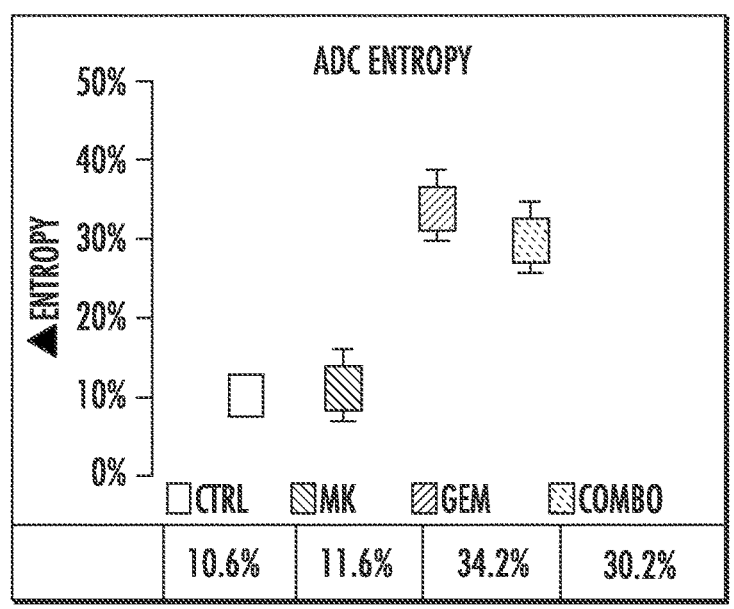
Figure 15:
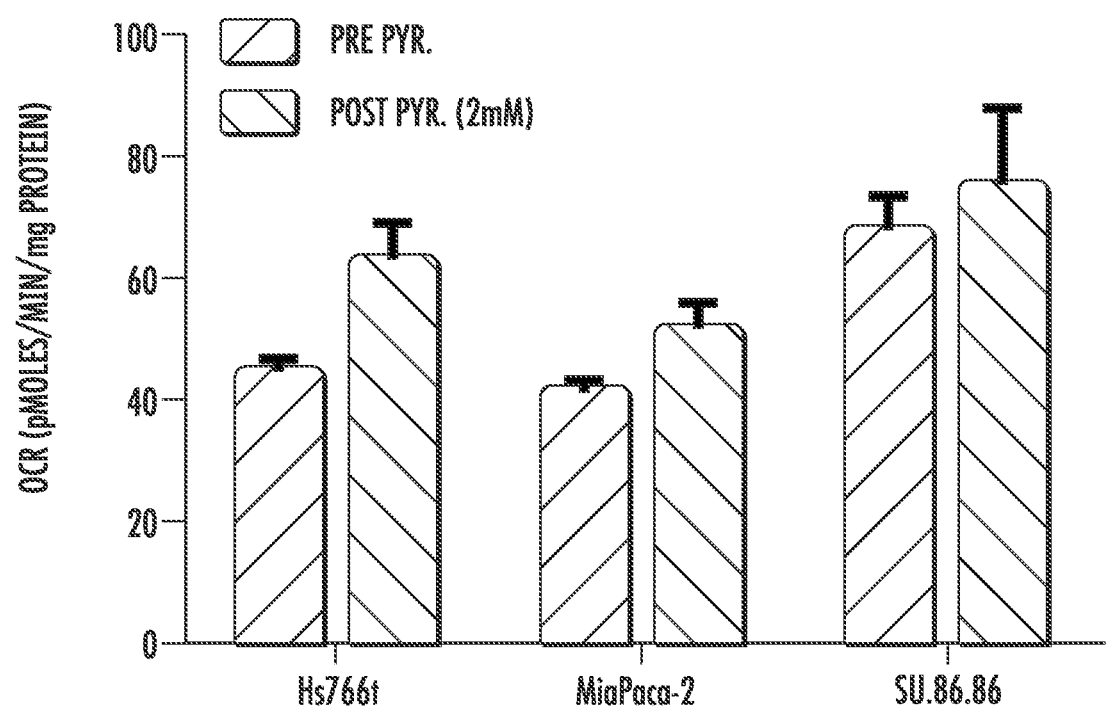
FIG. 15. Oxygen consumption increases in response to 2 mM pyruvate in Hs766t, MiaPaCa and Su.86.86 PDAC cell lines.
Figure 16:
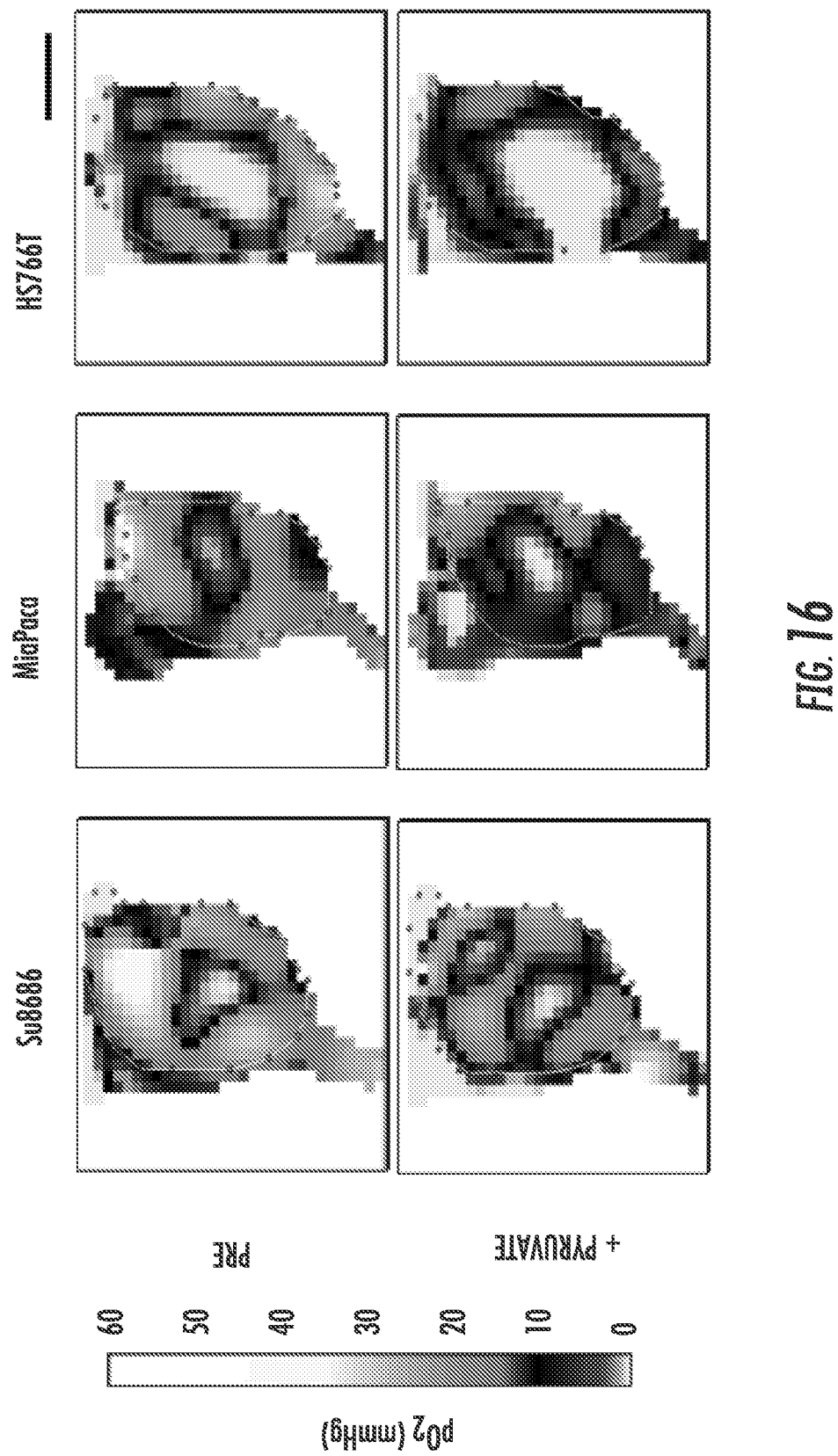
FIG. 16. Decreased intratumoral oxygenation 1 hr following 2 mmol/kg pyruvate in PDAC xenografts.
Figure 17:
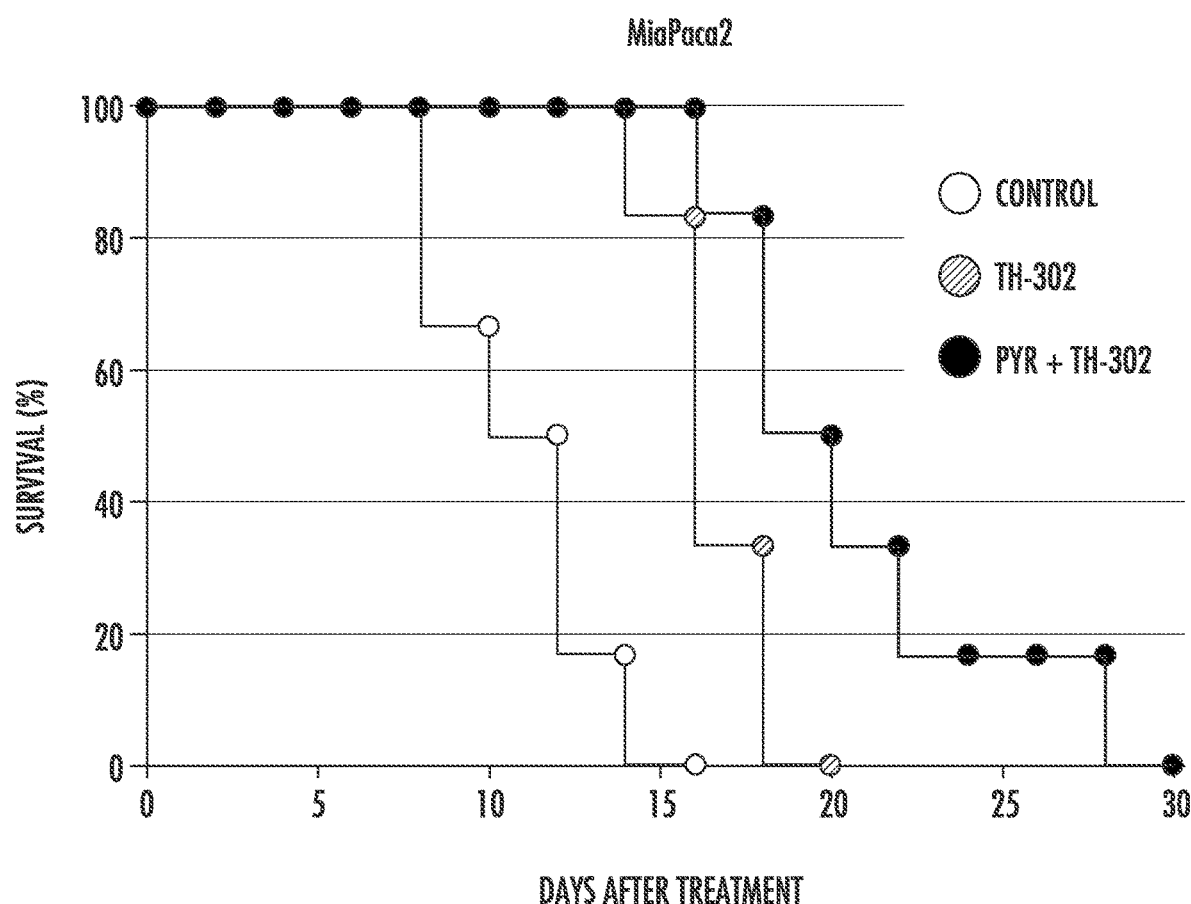
FIG. 17. Pyruvate improves survival associated with TH-302 therapy in MIA PaCa-2 xenografts FIG. 18. (A) T2w Axial slice (B) Early enhancement DCE (C) tumor contrast-to-time pattern; (D) ADC map; (E) Volumes of high perfusion (red) and low ADC (yellow) displayed in MIM.
Figure 18A:
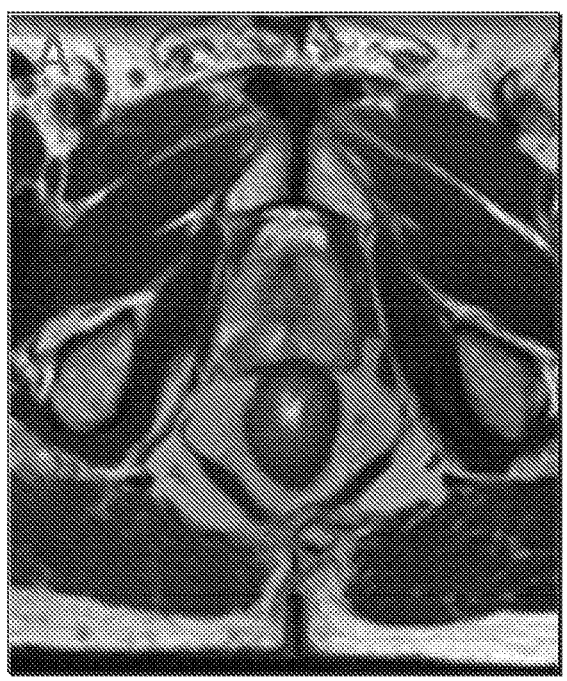
Figure 18E:
Figure 18B:
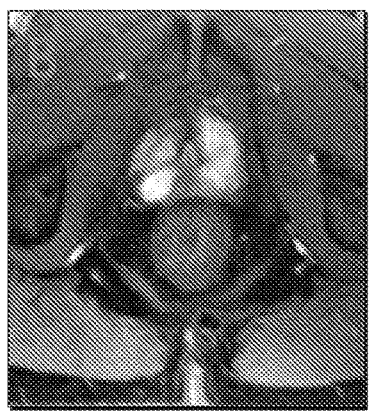
Figure 18C:
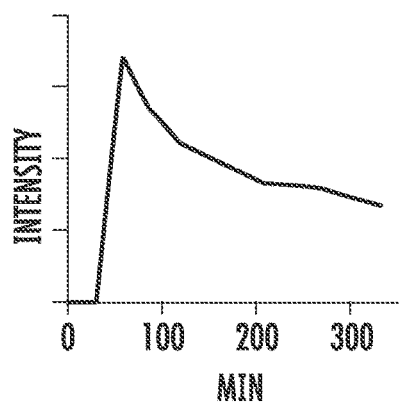
Figure 18D:

At a deeper level of analysis, the ADC maps were analyzed for image entropy, which is calculated as the randomness of a 3×3 pixel matrix surrounding the pixel under test (P-U-T). Maps of ADC-Entropy for each treatment group are shown in FIG. 14A, and show that all tumors have entropically definable "habitats". FIG. 14B shows that there were significant differences in the habitat distributions between tumors that responded to therapy (Gem and Combo) compared to those that did not (Ctrl and MK1775).

Example 3

Prostate Cancer

Methods

Active Surveillance:

Prostate cancer is often over-treated, as many men will not become symptomatic or die from their disease. As has been described by the Urology group at the University of Miami, active surveillance (AS) is an attractive alternative to primary therapy with total prostatectomy or radiotherapy, buying time to determine if the disease needs to be treated and preserving function in many patients for over 5 years [Soloway M S, et al. European urology. 2010 58(6):831-835; Klotz L. Pro. J Urol. 2009 182(6):2565-2566; Soloway M S, et al. BJU Int. 2008 101(2):165-169]. The postponement of treatment and preservation of quality of life is of primary importance, particularly for men in their 50's and 60's. Since men in these age ranges most often have a long life expectancy, it is imperative that the window of opportunity for cure be preserved.

Older surveillance studies in the pre-PSA era have documented the natural progression of prostate cancer, illustrating the metastasis and mortality risks. Death due to prostate cancer occurs late, but is significantly greater in men observed versus those treated primarily [Bill-Axelson A, et al. J Natl Cancer Inst. 2008 100(16):1144-1154]. The key is to determine early those who are not good candidates for active surveillance. Recent reports show a 22-30% rate of conversion to treatment by 2-3 years. The men who require early conversion are probably those who have been under-staged and/or undergraded by conventional assessments.

MP-MRI of the Prostate:

T2w MRI provides an excellent depiction of prostate anatomy with lower signal intensity in prostate cancer [Hegde J V, et al. J Magn Reson Imaging. 2013 37(5):1035-1054]. Diffusion Weighted Imaging (DWI) is sensitive to water molecule diffusion and the derived Apparent Diffusion Coefficient (ADC) values are significantly lower in tumor than in normal prostate due to restricted water diffusion. The lower the ADC value, the greater the chance of diagnosing Gleason score (GS) 7 disease [Vargas H A, et al. Radiology. 2011 259(3):775-784 Somford D M, et al. Invest Radiol. 2013 48(3):152-157; Peng Y, et al. Radiology. 2013 267(3):787-796]. Dynamic contrast enhanced (DCE)-MRI has also been applied to discriminate normal from malignant prostate tissues, with earlier and greater enhancement followed by washout seen in the latter. DCE-MRI measures vascularity and hence angiogenesis. Both DWI and DCE have a relatively high sensitivity and specificity for prostate cancer [Vargas H A, et al. Radiology. 2011 259(3):775-784 Mazaheri Y, et al. Radiology. 2008 246(2):480-488; Schmuecking M, et al. Int J Radiat Biol. 2009 85(9):814-824; Isebaert S, et al. J Magn Reson Imaging. 2013 37(6):1392-1401]. MP-MRI that includes T2, T1 non-contrast, DCE-MRI, and DWI sequences results in higher sensitivity, specificity and accuracy of tumor localization [Isebaert S, et al. J Magn Reson Imaging. 2013 37(6):1392-1401; Sciarra A, et al. Eur Urol. 2011 59(6):962-977].

Transrectal Ultrasound (TRUS) and MRI Targeted Biopsies in Active Surveillance Patients:

Prostate cancer is often multifocal and heterogeneous and thus presents a challenge in identifying biopsy sites. Transrectal Ultrasound (TRUS) guided biopsy remains an imprecise technique with 30% or more of prostate tumors being isoechoic [Shinohara K, et al. J Urol. 1989 142(1):76-82] and a roughly 50:50 chance of documenting cancer in hypoechoic lesions [Gosselaar C, et al. BJU Int. 2008 101(6):685-690]. Since the biopsy needle cannot be directed reliably to a tumor focus, a grid-like systematic biopsy of the gland is now routine. Highest grade and/or volume lesions are often missed. MRI-guided prostate biopsies via MRI-ultrasound (MRIus) fusion or biopsies done directly on an MRI yield a higher proportion of positive biopsies, especially from regions of low T2 intensity, low ADC values and high early contrast enhancement.

Radiomics:

Radiomics data are in a format that is amicable for building descriptive and predictive models relating image features to outcome, as well as gene-protein signatures. Resultant models may include imaging, molecular, and clinical data, and provide valuable diagnostic, prognostic or predictive information. Image features has been used by others to relate MRI or CT image features to global gene expression patterns in glioblastoma multiforme (GBM) and hepatocellular carcinoma (HCC) [Diehn M, et al. Proc Natl Acad Sci USA. 2008 105(13):5213-5218; Segal E, et al. Nat Biotechnol. 2007 25(6):675-680]. Image texture features in CT of the lung that are prognostic of survival have been developed [Basu S, et al. 2011 1eee International Conference on Systems, Man, and Cybernetics (Smc). 2011:1306-1312]. These methods are semi-automated wherein the radiologist identifies the lesion and computer software proceeds to segment, render and generate a report of quantitative features. These reports are pertinent to the questions: Which features are informative (e.g. have a wide range and are measurable in all samples)? What is the variance from one measurement to another and what are the critical sources of that variance? Are the features with largest dynamic range related to outcomes?

As disclosed herein, specific "habitats" from radiological images can be used with radiomics for prostate cancer analysis [Gatenby R A, et al. Radiology. 2013 269(1):8-15]. This approach involves the combination of co-registered images from multiple modalities, with each one contributing a piece of orthogonal information. For this reason, MRI is a technique of choice because multiple pieces of co-registered orthogonal data can be generated in a single exam. For example, DCE-MRI is a powerful method to identify regional distributions of blood flow, and lack of blood flow. The texture of these enhancements have proven to have significantly higher prognostic value than simple region-of-interest (ROI) measures. Diffusion MRI measured ADCs is a powerful method to interpolate the density of diffusion barriers (i.e. cells) and hence provides information that may be biologically, but not physically, related to DCE. T2 is sensitive to microscopic perturbations in the magnetic field; this is affected by blood flow and cell density, but in a non-linear fashion. Hence, T2 information is not strictly orthogonal to DCE and ADC and this correlation is accommodated in habitat imaging.

Results

MP-MRI and Active Surveillance.

In some cases, the practice is to classify suspicious imaging tumor volume regions (SImTVs) as dominant or nondominant using semi-quantitative methods, and describe tumor location and extent from the intersection of three spatial maps: (i) DCE-MRI based on tumor pattern weight $W_T>\text{mean}(W_T)+\text{stdev}(W_T)$ and (ii) DWI determined by ADC<1,000 µm$^2$/s, and (iii) T2w intensity. Dominant SImTV(s) will have a hypointense T2w lesion corresponding with the highest $W_T$ and lowest ADC values. Any other combination with pathologic confirmation would be considered nondominant. Persistence of disease in the dominant lesion is a common mechanism responsible for progression [Pucar D, et al. Int J Radiat Oncol Biol Phys. 2007 69(1): 62-69]. Suspicious dominant and nondominant tumor volumes will be targeted for MRI-directed biopsies.

Figure 19:
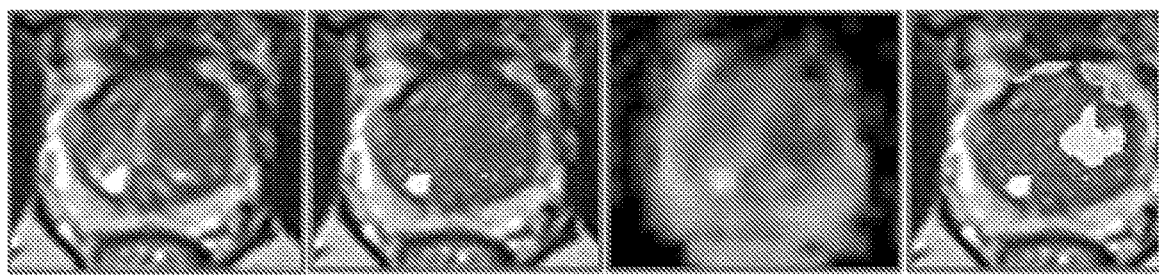
FIG. 19. (left to right) Axial slice of prostate on T2w; DCE map; ADC map; Combination with low ADC values (green) and ADC-DCE overlap in yellow, displayed in MIM.

The integrated platform for SImTV visualization and analysis uses MIM Software Inc (Cleveland, Ohio, USA). Using MIM extensions, an unsupervised pattern recognition technique is implemented for identification and automatic delineation of SImTVs in the DCE-MRI (FIG. 18). The approach is based on non-Negative Matrix Factorization (NMF), described in detail in Stoyanova et al [Stoyanova R, et al. Transl Oncol. 2012 5(6):437-447]. Briefly, the DCE-MRI data matrix D (containing the individual pixel contrast-to-time curves in rows) is represented as a product of k basic contrast signatures S(t) and their weights W(X), i.e. D~W×S under the constraint that all elements of W and S are non-negative. The tumor area is characterized with rapid uptake followed by continuous washout of the contrast (FIG. 19C). The weights $W_T$, corresponding to this contrast-to-time pattern represent the DCE-tumor map and after applying threshold=mean($W_T$)+stdev($W_T$), a tumor volume is created (FIG. 19E, red). Here and in the rest of the text we will refer to $W_T$ as $DCE_T$. Low ADC values (e.g., <1000 s/mm$^2$ has been used, but this is selectable) are also auto-contoured in MIM (FIG. 19E, red-green overlap is yellow).

Using this procedure, 65 consecutive patients (pts) were analyzed and SImTVs identified in 83% (n=54) [Stoyanova R, et al. International Journal of Radiation Oncology Biology Physics. 2011 81(2):5698-5699]. The SImTVs were 0.3 to 11.7 cc (mean±SD: 2.9±2.7 cc and median=1.85 cc). Prostate volumes were 40.1±20.9 cc (median=34.7, range=14 to 111.2 cc). Peripheral zone (PZ) volumes were 10.1±4.8 cc (median 9.3, range 2.5 to 27.6 cc. SImTVs were on average 8% and 30% (median 6% and 22%) of the prostate and PZ volumes. SImTVs were detected in the PZ, central gland (CG; also called transition zone or TZ) or both in 34 (63%), 11 (20%) and 9 (17%) of pts, respectively. ADC maps improve the differentiation of malignant from benign tissue, especially in the TZ [Jung S I, et al. Radiology. 2013], in which associated inflammation is a confounding factor on DCE-MRI. ADC maps (FIG. 19), in combination with T2w intensity compliment DCE and improve TZ tumor localization [Jung S I, et al. Radiology. 2013].

Figure 20:
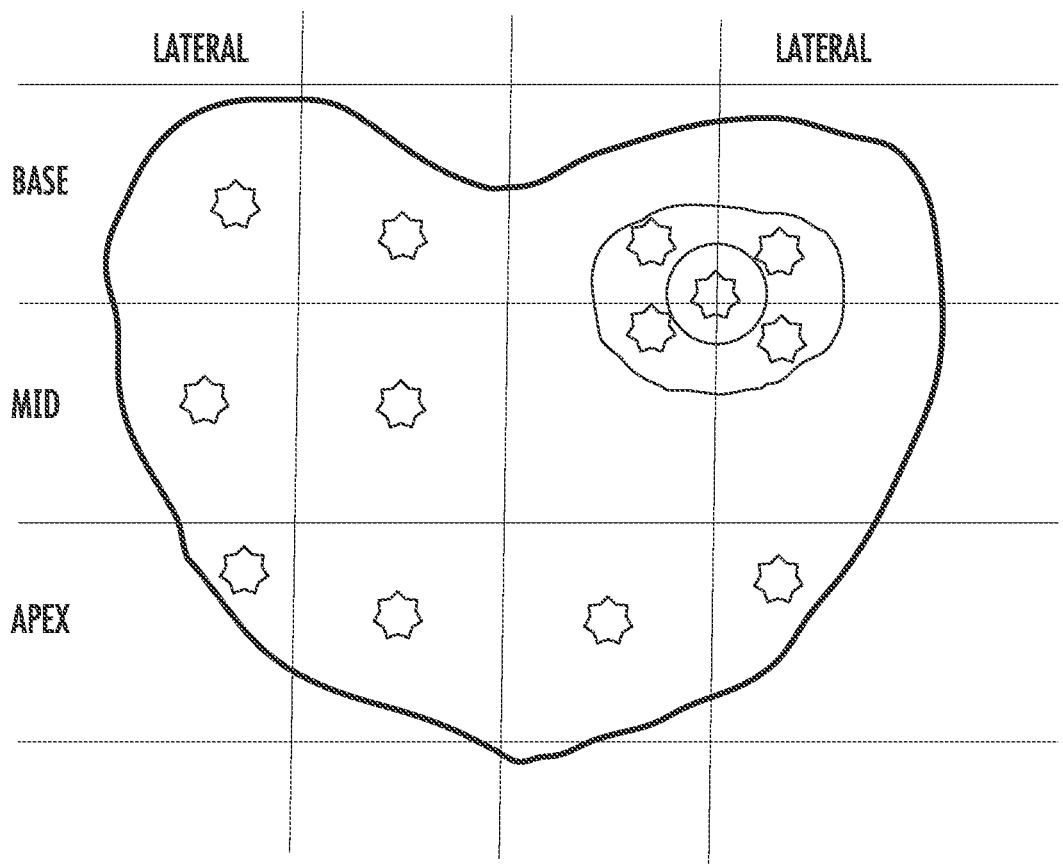
FIG. 20. Schematic representation of the prostate and the biopsy locations. The shaded area in the upper right of the prostate contour depicts the SImTV. The symbols in blue represent the location of biopsy sampling in the regions not suspicious for tumor. Note that in the regions suspicious for tumor, the biopsies will target the suspicious lesion (red symbols). The green represents an extra biopsy from this area (up to 14 biopsies permitted).

MRI-Ultrasound (MRIus) Fusion for Targeted Prostate Biopsies:

MP-MRI—ultrasound image fusion (MRIus) in the Artemis™ system (Eigen, CA) improves the rate of positive biopsies [Abazov V M, et al. Physical review letters. 2011 107(12):121802; Sonn G A, et al. J Urol. 2013 189(1):86-91]. A 3D TRUS is acquired just prior to biopsy by reconstructing sweeps of 2D to 3D. Both of these volumes are subject to a semiautomatic segmentation [Li B S, et al. 2002 47(3):439-446] that involves the specification of four or more points along the gland boundary (FIG. 20). The original 3D TRUS volume and warped MRI volume are both readjusted to correspond to the real time 2D ultrasound image. FIG. 21 illustrates a case in which an anterior lesion was identified in a patient being considered for active surveillance. The MRIus biopsy confirmed high volume GS 7 disease. Subsequently, the patient received radiation treatment.

MP-MRI and MP-MRI-guided prostate biopsies have identified a number of active surveillance (AS) patients with anterior or lateralized lesions that were contained Gleason grade 4-5 disease, who were originally thought to be ideal candidates for AS, and our findings are in concordance with others who have used these approaches [Stamatakis L, et al. Cancer. 2013 119(18):3359-3366; Hoeks C M, et al. Invest Radiol. 2013].

Methods

MP-MRI Habitats in the Prostate.

Figure 22:
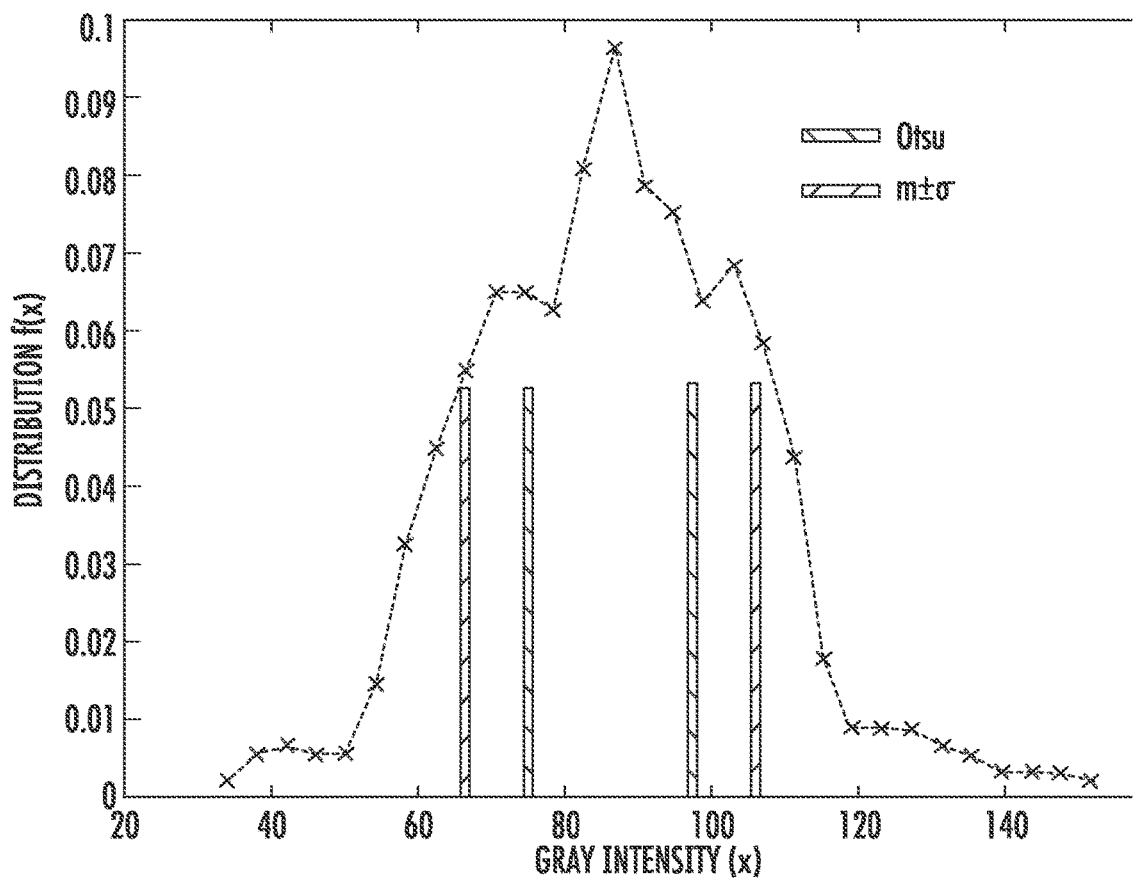
FIG. 22. Histogram of the T2 intensities in the prostate of a patient with prostate cancer. Otsu and mean±σ thresholds.

The MP-MRI prostate exam is composed of three modalities which represent anatomy, cellularity and blood flow. Tumor is typically identified by a trained radiologist, looking at each modality and contrast phases manually. Other imaging regions, however, are not identified in this analysis. The contiguous regions across a modality based on a given criterion are referred to as habitats. A computational method is proposed to connect three modalities (T2, DWI and DCE) to find regions of interest that will characterize the prostate beyond the tumor location. The habitats are identified separately in PZ and Central Gland (CG) because of different imaging characteristics of the prostate zones (FIG. 22).

Let $I_{T2}$, $I_{ADC}$ and $I_{DCE}$ be the image in R$^2$ space for the T2, ADC and $DCE_T$, resp. For simplicity, the approach is described for a single slice with square FOV (n×n). The three modalities are registered with MIM Software which provides high level of accuracy of alignment. Two Regions of Interest (ROIs): Prostate and Peripheral Zone (PZ) are manually contoured in MIM. The pixels within the prostate are classified in three groups based on the distribution of the pixel intensity. There are optimal methods for distributional delineation; the most popular to find an optimal cutoff is the Otsu threshold method [Sezgin M, et al. Journal of Electronic Imaging. 2004 13(1):146-168]. In this approach, the subpopulation obtained by the categorization is called high, low and uncertain with respect to the pixel intensities. The pixels of interest across modalities are the ones that correspond to the common region of interest, which can be written as the intersection of the regions.

$$\Psi = I_{T_2}(i,j) \cap I_{ADC}(i,j) \cap I_{DCE_T}(i,j), \qquad (e.1)$$

where the intensities in each modality satisfies the following conditions:

$$I_{T2}(i,j) \leq \theta_{T_2}; I_{ADC}(i,j) \leq \theta_{ADC}; I_{DCE_T}(i,j) \geq \theta_{DCE}; i,j=1,\ldots,n.$$

Figure 23:
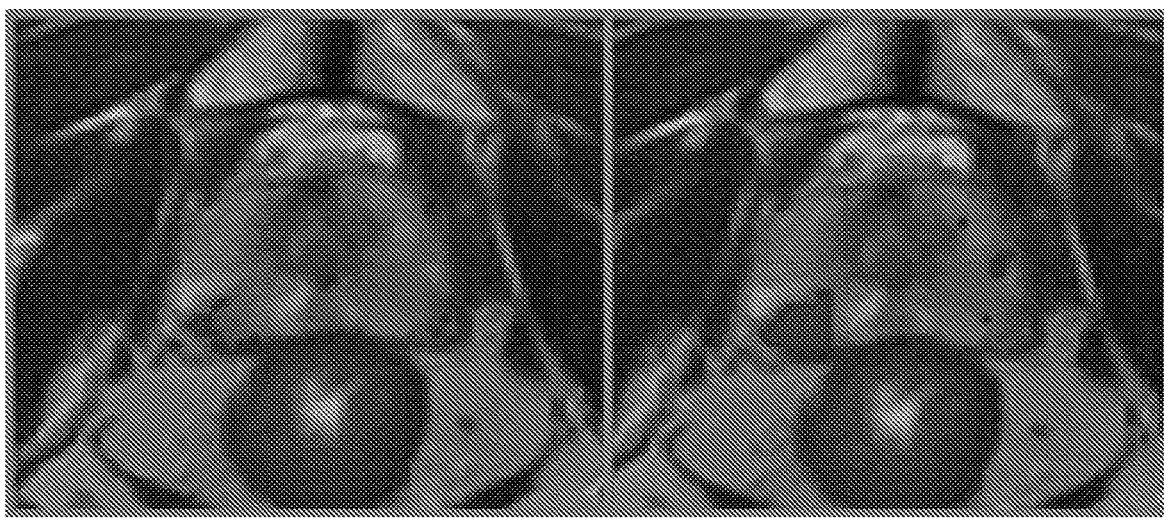
FIG. 23. Habitats, based on intersections between the T2, ADC and DCE (left) and ADC and DCE (right).
Figure 24:
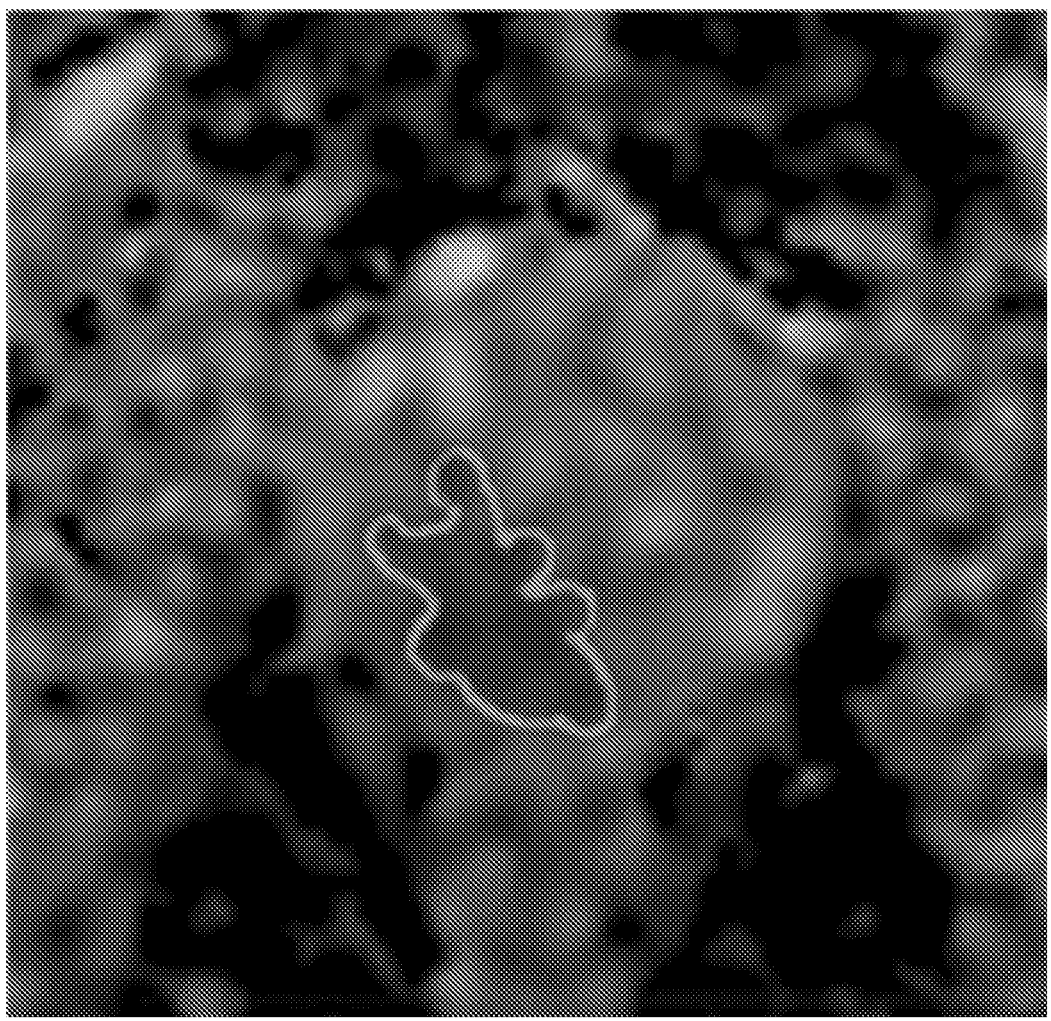
FIG. 24. An irregular shaped tumor on ADC map.

$\theta_{T2}$, $\theta_{ADC}$ and $\theta_{DCE}$ are the cutoffs for high or low habitats in T$_2$, ADC and $DCE_T$ image of size n×n. The same conditions could be translated to the entire tumor by taking all the slices for the region of interest. FIG. 23 shows the distribution of pixels in the sample case, with vertical lines corresponding to possible cutoffs. An example of habitats are shown in FIG. 24. In this patient there was no overlap in CG based on the three criteria (Eq. 1). Prostate biopsies are placed in reference to the dominant and nondominant SImTVs identified. The biopsy histopathologic results (i.e., percent core tumor tissue, GLSC and percent Gleason grade 4) will then inform on the relevance of the habitat(s).

Radiomics of Prostate Habitats.

Radiomic image features are extracted from each of the identified habitats. These features describe characteristics of the image intensity histograms (e.g., high or low intensity), tumor shape (e.g. round or spiculated), texture patterns (e.g. homogeneous or heterogeneous), as well as tumor location (PZ, CG). Several types of image features can be extracted to describe the tumor's heterogeneous shape and structure. Note there are multiple features extracted in some of the categories. Texture features have been shown to be good descriptors of the tumor and have shown relevance for survival prediction [Basu S, et al. IEEE Systems Man and Cybernetics. Anchorage: IEEE Systems Man and Cybernetics. 2011]. The list of the features (Table 8) is expanded based on 219 custom 3D image features developed for lung CTs [Basu S, et al. 2011 Ieee International Conference on Systems, Man, and Cybernetics (Smc). 2011:1306-1312]. Using the contoured volumes for the prostate and PZ, as well as the identified tumor and other habitat(s), the volume descriptors are calculated (C1, TABLE 9). Quantitative features describing the geometric shape of the tumor can also be extracted from the 3D surface of the rendered volumes (C2, Table 8). For example, the surface-to-volume ratio can be determined, where a tumor with irregular form (FIG. 24) has a higher value than a round tumor with a similar volume. Category C3 describes tumor location (PZ, CG and PZ/CG). Intensity histogram based features (C4, Table 8) reduce the 3D data into a single histogram and common statistics for each region/modality can be calculated (e.g. mean, median, min, max, range, skewness, kurtosis). Co-occurrence matrix features are widely used for texture classification (C5, Table 8). The joint conditional probability density function $P(i,j;a,d)$ is in the basis of co-occurrence matrix: the elements $(i,j)$ represent the number of times that intensity levels i and j occur in two voxels separated by the distance d in direction a. Subsequently, from this conditional probability density function, features can be extracted, e.g., describing autocorrelation, contrast, correlation, cluster prominence, cluster shade, cluster tendency, dissimilarity, energy, homogeneity, maximum probability, sum of squares, sum average, sum variance, sum entropy or difference entropy, etc. Further, gray level run length features are extracted. A gray level run is the length, in number of pixels, of consecutive pixels that have the same gray level value. Most size and shape based feature computations will be implemented within the Definiens XD® platform (Munich, Germany), while texture and other derived features are computed from algorithms implemented in C/C++.

TABLE 8

Broad radiomics feature categories

| Cat. | Name | Description | Modality | PZ | CG | Tumor | Habitat | Total |
|------|------|-------------|----------|----|----|-------|---------|-------|
| C1 | Region Size | Volume Descriptors | T2w | X | X | X | X | 5 |
| C2 | Region Shape | Roundness/irregular descriptors | T2w | | | X | X | 24 |
| | | | CE-T1 | | | X | X | 24 |
| | | | ADC | | | X | X | 24 |
| C3 | Tumor Location | PZ, CG | T2w | X | X | X | X | 6 |
| C4 | Pixel Intensity | Histogram of Intensity | T2w | X | X | X | X | 24 |
| | | | ADC | X | X | X | X | 24 |
| | | | $DCE_T$ | X | X | X | X | 24 |
| C5 | Grayscale: | Run length and Co-occurrence patterns | T2w | | | X | X | 34 |
| | | | ADC | | | X | X | 34 |
| | | | $DCE_T$ | | | X | X | 34 |
| C6 | Wavelets | Wavelet kernels (entropy and energy) | T2w | | | X | X | 60 |
| | | | ADC | | | X | X | 60 |
| | | | $DCE_T$ | | | X | X | 60 |
| Total | | | | | | | | 432 |

Reproducibility of Image Features:

As expected, the radiomics approach generates hundreds of variables, some of which may be redundant. In addition, the numbers of extracted features can be higher than the number of samples in the study, reducing power and increasing the probability of overfitting the data. In the prior CT study, a combination of ad hoc methods for dimensionality reduction was used for reproducibility. In this proposal, we will apply a similar approach for selection of features, that are highly reproducible, informative and non-redundant. First, using test-retest prostate image dataset, highly reproducible features will be selected based on the concordance correlation coefficient, CCC, with a cutoff of 0.90 for high reproducibility. Subsequently, the CCC-prioritized features will be analyzed for dynamic range, calculated as the ratio of scalar biological range to the test-retest absolute difference. Features showing high dynamic range are considered to be informative. A dynamic range of can be arbitrarily used as a cutoff, although features with lower dynamic range may also be informative. Finally, the redundancy in the features, selected after passing through reproducibility and dynamic range requirements, can be reduced by identifying highly correlated features based linear dependency measured by coefficient of determination ($R^2$) across all samples. An $R^2>0.95$ is considered to be highly redundant and thus can be combined into a single descriptor. In the lung CT set, the serial application of these three methods reduced a set of 219 features to 48 features that were reproducible, informative and not redundant ($R^2<0.95$, CCC$\geq$0.90).

Statistical Analysis:

To perform feature selection of high-throughput MP-MRI radiomics in habitats associated with adverse histologic parameters and biofluid markers PSA, PCA3 and pro-PSA. A two-stage feature selection approach can be used. In the first step radiomics variables can be filtered out using standard univariate analysis (t-test or ANOVA) and in the second step tree based classification (like random forests) can be performed to identify radiomics signatures of habitats in relation to risk groups. The predictive performance of radiomics signature can be evaluated using misclassification error rate of out-of-bag ($MER_{OOB}$). Random forests methodology can be used to identify radiomics features correlated to PSA, PCA3, and pro-PSA.

Digital Histology.

Figure 25:
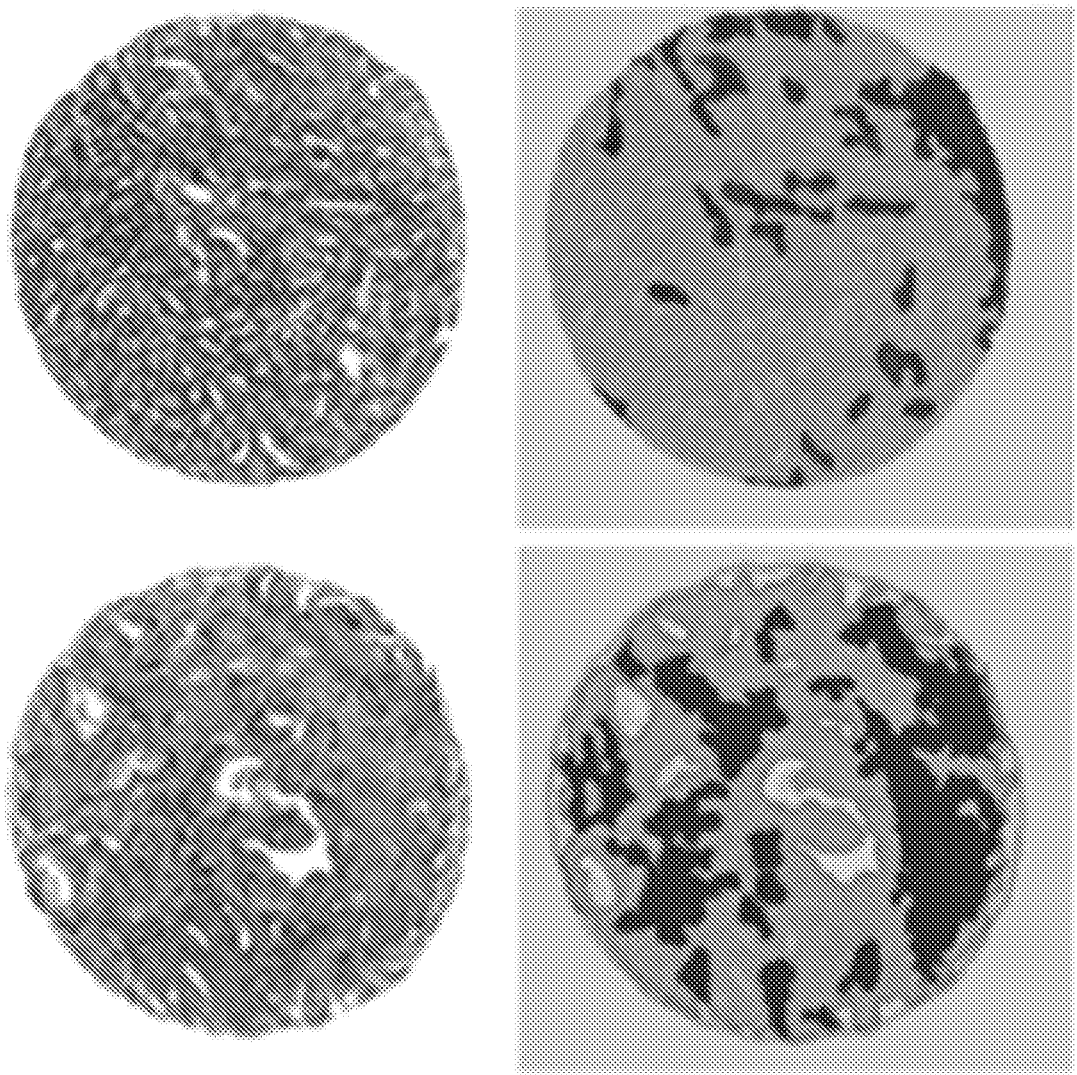
FIG. 25. QH of Prostate Cancer. Two Gleason 6 core biopsies were analyzed by segmenting individual cells from H&E images (left) and classifying them (right) as stroma (blue) or cancer (orange) illustrating range of stromal involvement.

The histology pattern recognition technology suite Tissue Studio v3.0 (Definiens, Munich, Germany) can be used as a customized tool to identify tumor regions of interest and segment cancer from the surrounding tissues before segmenting single cells within the tumor regions for each digital slide. In H&E cells will be analyzed for evidence of distinct morphologies. This is accomplished by analyzing the 34 morphological features that can be discriminated by Otsu thresholding as "low" or "high", and these are combined into 2×2, 3×3 or 4×4 matrixes to define 4, 9 or 16 distinct "morphotypes" wherein cells within each are expressing similar combinations [Lloyd M C, et al. J Pathol Inform. 2010 1:29]. Morphotypes generally cluster into spatially distinct regions ("microhabitats"). Stroma often, but not always, presents with a common morphotype, whereas the cancer cells commonly exhibit 4 or 5 distinct clusters. FIG. 25 is an example of two Gleason grade 6 core biopsies that have different levels of stromal involvement, which can be prognostically important [Basanta D, et al. British journal of cancer. 2012 106(1):174-181]. For IHC, each cell can be classified by software based on the biomarker intensity into quintiles, representing from 0 to 4+staining. Heatmaps of the resulting expression patterns can further identify clusters or microhabitats, that are related to the H&E data.

Predictive Feature Modeling.

In this study advanced imaging (Radiomic, R), histological (Digital Pathology, P) and clinical (Genomic markers, other clinical parameters like PSA, Gleason score etc, C) could be used in the predictive model to find a therapeutic score r, which is a real value (could also be binarized into Yes/No with a unbiased midpoint cutoff), which is written as, $$\tau = f(Radiomic, Pathology, Clinical)$$

The function could be linear or non-linear based on the sample size and feature set. In linear settings, say $n_1$, $n_2$, $n_3$ are subset of informative features derived in Radiomics, Pathology and Clinical respectively, the above functional could be written as:

$$\tau = \Sigma_{i=1}^{n_1} \alpha_i R_i + \Sigma_{i=1}^{n_2} \beta_i P_i + \Sigma_{i=1}^{n_3} \gamma_i C_i$$

Where α, β and γ are optimal weights. The informative features in each category would be obtained by finding best predictive feature in the training set. Using the High performance computing best n-dimensional feature can be obtained (limited by the computing power, unfettered access to Moffitt 696 core HPC). Conventional support vector, naïve Bayes, K-NN type class prediction methods could also be attempted to contrast the estimates. In order to make unbiased inference, synthetic samples were generated following the distribution of the sample groups has been studies in classification [Kim S, et al. J Comp Biology. 9(1):127-146] and contrasting with popular error estimates [Braga-Neto U M, et al. Bioinformatics. 20(2):253-258]. The model can be trained using subsampling methods [Hua J, et al. EURASIP J Bioinform Syst Biol. 2006 2006 (1)] and errors of the predictor estimated using the series of cross validation & sample spreading methods appropriate for small samples will be attempted.

Example 4

Pancreatic Cancer

Cell Lines and Xenografts:

MIA PaCa2, BxPC-3, PANC-1, SU.86.86, Hs766T can be purchased from ATCC. Primary tumors can be generated by Ultrasound (US) guided implantation of 5e5 cells into pancreata of nu/nu mice, as in [Huynh A S, et al. PLoS One. 2011 6(5):e20330], and some of these develop hepatic metastases.

Figure 26:
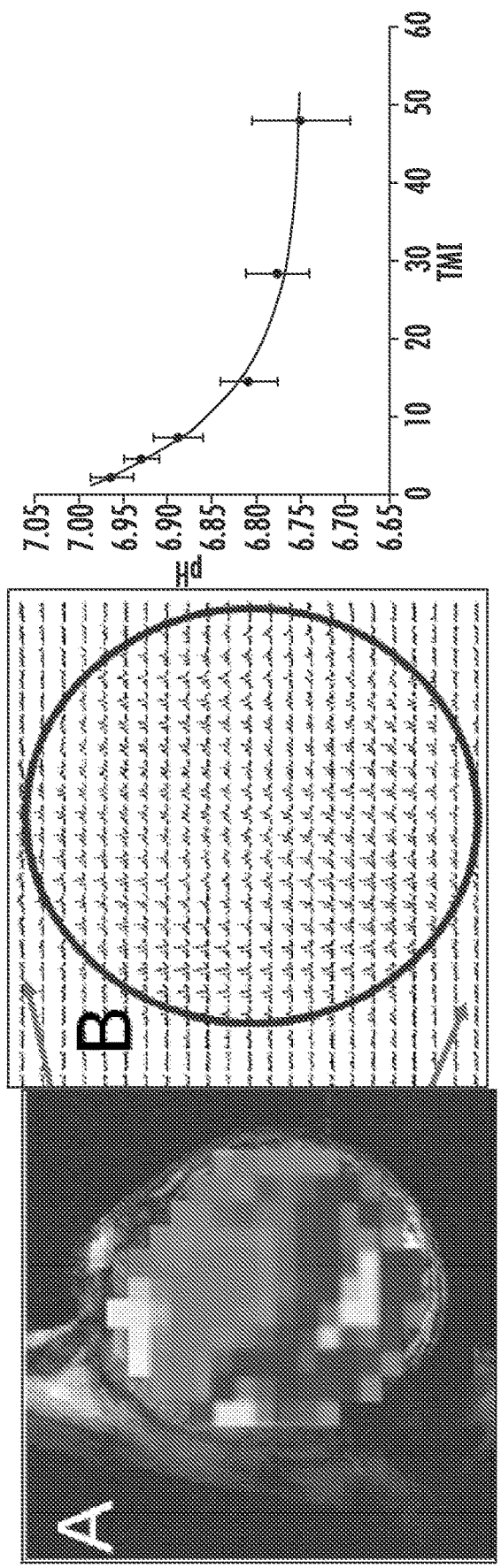
FIG. 26. pH imaging. (A) pH image from MRSI of IEPA of MDA-mb-435 mouse xenografts, overlaid on contrast-enhanced image of same. (B) CSI matrix obtained 20-40 mins after injection of IEPA, delineating region of tumor in red circle. (C) from co-registered DCE and pH data, relationship between pHe to the time to maximal intensity, TMI, showing lower pH with less perfusion.

KPC Mouse Model:

There are 15 genetically modified mouse models (GEMM) of PDAC. The KPC (KrasG12D; p53R172H; Pdx1-Cre) GEMM is widely used, well-validated, and clinically relevant [Olive K P, et al. Clin Cancer Res. 2006 12(18):5277-5287], although tumors in KPC mice are generally resistant to gemcitabine. KPC mice develop a spectrum of premalignant PanINs that ultimately progress to overt carcinoma with 100% penetrance. The tumors exhibit stromal desmoplasia, similar to human PDAC. Metastases occur in ca. 80% of KPC mice, primarily to the liver and lungs. Emergence of pancreatic lesions measurable by US occurs between 10-16 weeks and they can be monitored until they reach 200-300 $mm^3$, at which time they can be randomized into study.

pH Imaging with $^1$H MRSI of IEPA:

The pHe of tumor and stroma can be measured with $^1$H MRSI of the imidazole, IEPA [van Sluis R, et al. Magn Reson Med. 1999 41(4):743-750]. Outer volume suppression (OVS) can be used with pre-saturation water suppression followed by a standard MRSI pulse sequence to generate spectral maps in approx. 20 min of acquisition. FIG. 26 shows a pH image of MDA-mb-435 xenograft, along with the CSI matrix and a derived relationship between pHe and perfusion from the co-registered images. The spatio-temporal resolution of these acquisitions can be improved by performing the acquisitions with spectral-spatial pulses for solvent suppression and compressed sensing. It is estimated that the resolution can be reduced to 1×1×1 $mm^3$.

Histological & Immunohistochemical (IHC) Biomarkers:

The following IHC markers can be used. Pimonidazole (Hypoxyprobe®) is an accepted measure of tissue hypoxia. In hypoxia, cells express hypoxia inducible factor, HIF1-α, which in turn induces expression of glucose transporter (GLUT-1) (89-91), and carbonic anhydrase IX (CA-IX) (51). GLUT-1 is associated with increased glucose metabolism, FDG uptake and poor prognosis [Behrooz A, et al. J Bio Chem. 1997 9:5555-5562; Airley R, et al. Clinical Can Res. 2001 7:928-934; Boado R J, et al. J Neurochemistry. 2002 80(3):552-554]. CA-IX catalyzes the hydration of $CO_2$ to acidify the extracellular pH [Turner K, et al. British Journal of Cancer. 2002 1276-1282(86)] and is associated with decreased survival in multiple cancer types [Turner K, et al. British Journal of Cancer. 2002 1276-1282(86); Kaluz S, et al. Biochimica et Biophysica Acta. 2009:162-172; Koukourakis M I, et al. Clinical Can Res. 2001 7(3399-3403):3399]. Vasculature is determined with IHC for PECAM-1/CD31. Further, plasma membrane staining for LAMP-2 may be a good marker for acidic pH, and this marker can also be used. Patent vasculature can be labeled by injecting Hoechst 33342 one minute prior to animal sacrifice. Antibody evaluation and optimization of staining protocols have been published [Tafreshi N K, et al. Clin Cancer Res. 2012 18(1):207-219; Tafreshi N K, et al. Cancer Res. 2011 71(3):1050-1059]. Stained slides can be scanned using the Aperio™ ScanScope XT, as in [Wojtkowiak J W, et al. Cancer Res. 2012 72(16):3938-3947]. Definiens Developer XD can be used to segment up to 100,000 individual cells per slide. The algorithm can be applied to the entire slide's digital image to segment positive pixels of various intensities. The positivity can be quantified by the number and location of cells exhibiting positive stain as a percentage of total tumor cell count, using established thresholds and the resultant "heat maps" can group cells with common phenotypes.

Habitat Imaging.

As disclosed herein, "hypoxic habitats" should result from deficits in perfusion measured with contrast-enhanced MRI, and should have high cell density and be adjacent to necrotic volumes, as measured by diffusion MRI. An example is shown in FIG. 10, which shows hypoxic (purple) and necrotic (green) habitats in clinical (panel A) and sub-cutaneous (B) pancreatic cancers. In the animal studies, these data were quantitatively compared to pimonidazole staining as a "gold standard". MRI is routinely used in the workup of PDAC patients, according to NCCN guidelines. In addition, 18-FDG PET is obtained in the workup of PDAC patients at Moffitt as SOC, and thus, results from this study could have rapid clinical translation.

FDG PET.

PET/CT images can be obtained with a Siemens Inveon.

Hyperpolarized $HCO_3$ and Other Tracers.

Figure 27:
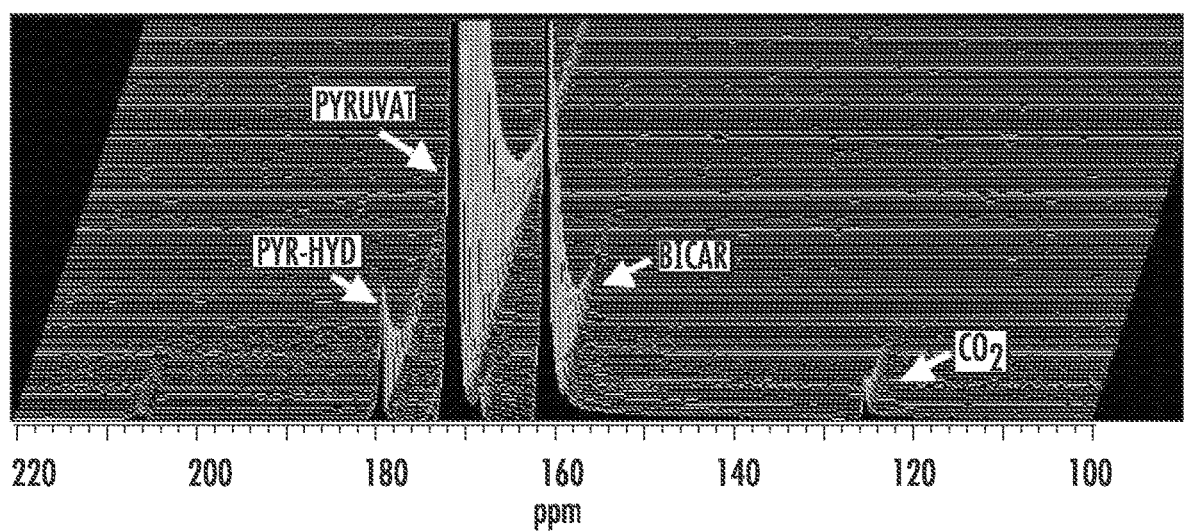
FIG. 27. Co-hyperpolarization of 13C bicarbonate and $^{13}$C-1-Pyruvic Acid. Stacks were generated from a series of 2 sec spectra showing decay of pyruvate (and hydrate) bicarb and $CO_2$.

An Oxford HyperSense DNP hyperpolarizer can be used for the hyperpolarization of $^{13}C$, $^{31}P$ and $^{15}N$ containing tracers. Published manuscripts include the use of $^{13}C$ pyruvate to evaluate inhibition of LDH-A and glutaminase [Dutta P, et al. Cancer Res. 2013] and the use of $^{13}C$ fumarate to evaluate the effects of sorafenib and the comparison of $^{13}C$ pyruvate metabolism to MRI measured diffusion to monitor anti-cancer therapy response [Zhang X, et al. Proc ISMRM. 2012 15:4049]. Additions include co-polarization of $^{13}C$ $NaHCO_3$ and $^{13}C$ pyruvic acid (FIG. 27), polarization of $^{31}P$ dimethylmethylphosphonate, DMMP, and polarization of $^{15}N$ glutamine.

General Protocol for Habitat Imaging:

Tumors are imaged at volumes between 300-500 mm³, first with MRI followed by 18-FDG PET. All animals have jugular catheters for reproducible injections and are anesthetized with isoflurane; respiration and temperature is monitored with Small Animal Instruments, Inc (SAII) monitoring system using a pressure sensitive respiration pad and a fiber optic rectal thermometer. The catheter can be fit with a 20 cm lead with a dead volume of 40 uL, allowing bolus injections of up to 160 uL (0.2 mL total). One day after the MRI scan, animals are injected with pimonidazole and FDG and imaged with PET using protocols that have been published previously [Cardenas-Rodriguez J, et al. Magn Reson Imaging. 2012; Morse D L, et al. NMR Biomed. 2007 20(6):602-614; Jordan B F, et al. Neoplasia. 2005 7(5):475-485] Immediately after capturing PET images, animals are sacrificed and tumors removed for whole mount histology and immunohistochemistry.

PET/CT Acquisition and Processing:

Dynamic imaging with Inveon PET/CT can be performed for 60 minutes starting at the injection of 250 μCi of $^{18}F$-FDG. Animal respiration and temperature can be monitored with an M2M Biovet system. SUVs are calculated by dividing the radioactivity per gram of tissues by injected dose of radioactivity per gram of mouse weight and expressed per 1×1×1 mm³ voxel. Time activity curves (TAC) will be generated using 150 sec frame durations and uptake rates can be calculated using Patlak analyses. Input functions, Cp(t), can be determined in a parallel series of animals by sampling 0.02 mL from the jugular vein at times throughout the 60 min uptake period.

MRI Acquisition and Processing:

Images and spectra can be acquired on a 7 Tesla ASR 310 horizontal system (Agilent Technologies, Inc.). Following scout images, animals can be injected via catheter with a 100 μL bolus followed by slow infusion of 175 mM Na-IEPA, pH 7.2 for the duration of the MRSI acquisition. These conditions yield maximal S/N without affecting the tumor pH through excess buffering [van Sluis R, et al. Magn Reson Med. 1999 41(4):743-750; Gillies R J, et al. IEEE Eng Med Biol Mag. 2004 23(5):57-64]. Improvements to the MRSI sequence can be made using spectral-spatial excitation for solvent suppression with Cartesian EPSI readout. These sequences and reconstruction software give a 16-fold acceleration factor compared to conventional MRSI. The benchmark for these studies is a SNR for the H2 of IEPA of >5 in 1×1×1 mm isotropic voxels with 2× zero-filled resolution enhancement within an acquisition time of 20 min. A full time series will be obtained as the IEPA infuses into the tumor to reach steady-state. Following pH imaging, a diffusion series can be obtained in 10 minutes with 4 b-values (50, 250, 500, 700), and a subsequent $T_1$ series can be obtained during which the animals are injected with a 0.1 mmol/kg bolus of Magnevist (50 uL+40 uL chase). DCE and DW images can be acquired with 0.25 mm in-plane and 1 mm slice resolution.

Image Co-Registration:

Image data can be imported into Matlab for all analyses. Tumors will be semi-automatically segmented from the $T_2$ and CT images using an ensemble segmentation approach that was developed [Gu Y, et al. Pattern Recognition. 2013 46(3):692-702]. $T_2$ MRI and CT images can be registered by generating volumetric surface maps from each modality and 3-D rotation to minimize differences using Dice coefficient as a similarity index. The rotation vectors can then be applied so that PET+CT+MRI are co-registered in subsequent analyses. Because PET resolution is lowest, the CT and MRI data can be down sampled to generate voxels of identical size, which is expected to be 1 mm isotropic.

Image Analysis and Algorithm Development:

This Example shows that a combination of contrast-enhanced MRI (as a marker for perfusion), diffusion MRI (as a marker for cellularity) and FDG-PET (as a marker for glycolysis) can be used to predict the pH of tumors. The dynamic contrast series can be analyzed to generate maps of the vascular transfer constant, $K_{trans}$, the vascular volume and the extravascular/extracellular volumes. From the $K_{trans}$ maps, volumes can be spatially defined that are well- and poorly-perfused. The diffusion series can be fit to the Stejskal-Tanner relationship [Jordan B F, et al. Neoplasia. 2005 7(5):475-485; Jennings D, et al. Neoplasia. 2002 4(3):255-262; Galons J P, et al. Neoplasia. 1999 1(2):113-117] to generate a 3-D volumetric map of the Apparent Diffusion Coefficient, ADC, using Levenberg-Marquardt nonlinear-least squares fitting [Foroutan P K, et al. PLoS One. 2013; Mignion L, et al. Cancer Res. 2013]. Dynamic PET data can be used to generate 3-D maps of per-voxel uptake rates, K, from Patlak analyses. Algorithms can be developed using continuous variables and, as the algorithms mature, and to make the analyses more clinically feasible, it is expected to be able to identify cutoffs for dichotomization [Otsu N. IEEE Trans Sys, Man, Cyber. 1979 9(1):62-66]. Also, for increased clinical applicability, it will be determined whether the same predictive value can be derived from: 15 minute post contrast enhanced data ($\Delta T_1$), a single (b=500) diffusion weighted image (DWI) and SUV values from the DCE, diffusion and PET data respectively.

"Habitat" Imaging.

Data cubes can be generated for each voxel with values for $K_{trans}$ (or $\Delta T_1$), ADC (or DWI) and uptake rates (or SUV). Analyses can be initiated using microPD, a suite of algorithms that predicts pharmacokinetics (PK) and pharmacodynamics (PD) using sample-specific histology images as input to the model [Rejniak K A, et al. Front Oncol. 2013 3:111]. Perfusion, cellularity, and glycolysis parameters obtained from each 1×1×1 mm$^3$ voxel in the PDAC "habitat" maps, can be used to predict the pH distributions, which are then quantitatively compared to the "ground truth" pHe values obtained from the $^1$H MRSI of IEPA which can be co-registered to the same samples. The model can be iteratively adjusted to maximize the correlation coefficient between predicted and measured pHe values. Upon completion of the test set, it is expected that the Bland-Altman CoV to be less than 15%. Additionally, these analyses can indicate whether there is bias in the errors toward extreme pH values, which are anticipated due to the titration curve of IEPA.

Histology and IHC:

Following imaging, animals can be injected i.v. with Hoechst dye and sacrificed, the tumors tattooed for orientation, formalin fixed and paraffin embedded as whole mounts. Initially, sections can be stained with H&E and IHC for pimonidazole and PECAM to identify hypoxia and vasculature, respectively. Fluorescent imaging of Hoechst dye can identify patent vasculature.

Example 5

Segmenting MRI Images of Brain into 3D Habitat Maps

Figure 28:
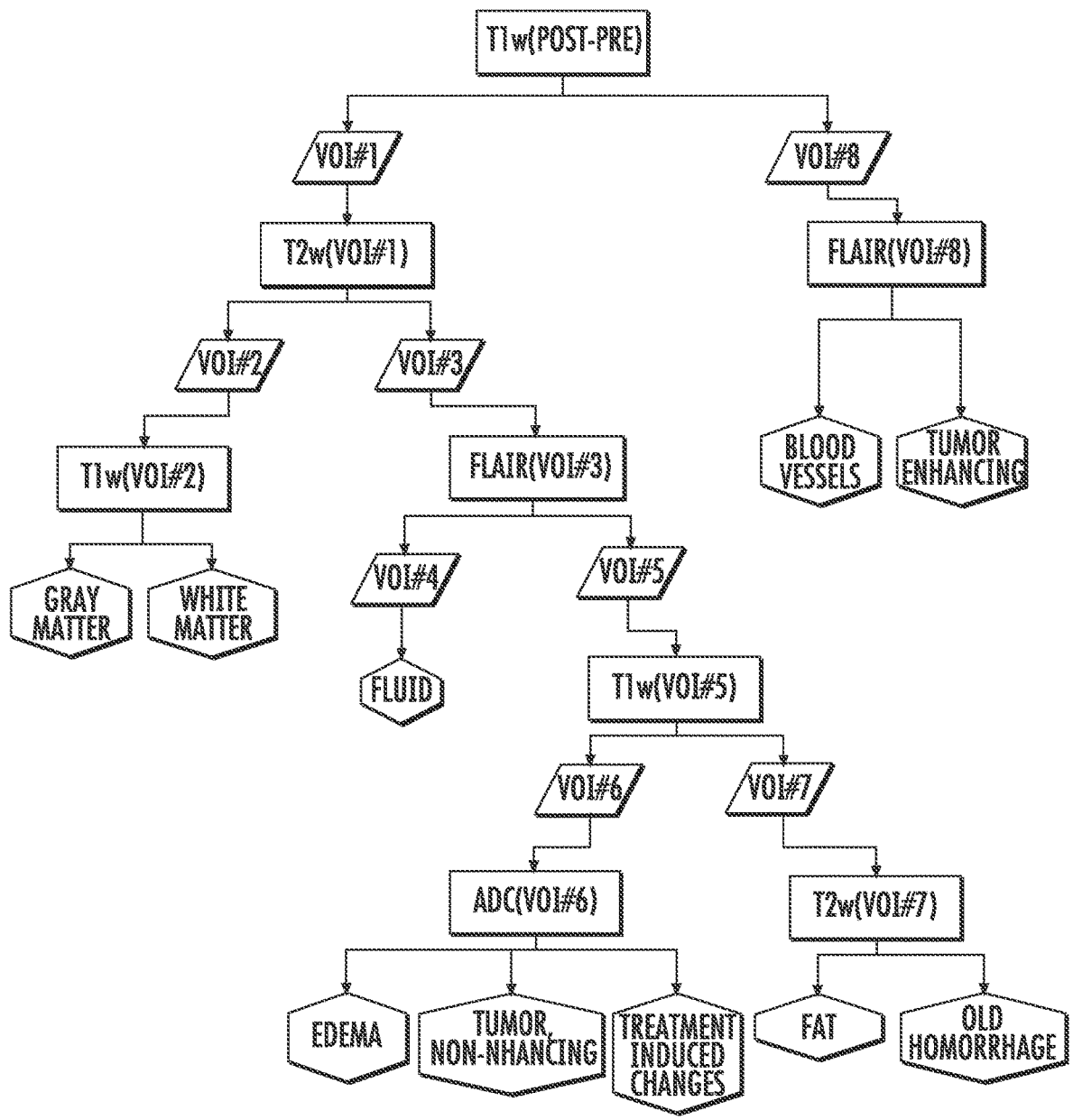
FIG. 28. Example decision tree using MRI sequences to identify distinct habitats within the entire brain. Co-registered T1-weighted pre-contrast, T1-weighted post-contrast, T2-weighted pre-contrast, FLAIR, and Apparent Diffusion Coefficient of water (ADC) maps and a binary brain mask were used as inputs to the algorithm depicted here. At each decision point in the algorithm, voxels are classified into either two or three clusters using Otsu thresholding. Note that the brighter clusters are shown to the right. Through the combination of MRI sequences, volumes of interest (VOIs) of the habitats were continuously refined, and a final habitat type identified for each of the 10 habitats in this decision tree.

The information contained in superimposable magnetic resonance imaging (MRI) images acquired using routine pulse sequences can be combined by a method such as depicted in FIG. 28 so as to permit objective 3D segmentation of the images to identify distinct normal and pathologic regions ("habitats") within organs, tumors and precancerous lesions. This knowledge-driven method can combine information from orthogonal MRI sequences to automatically segment the images into regions corresponding to habitats within organs based on the differential dependence of the relative signal intensity of each habitat on the MRI sequence used. This method will decrease the need for manual interaction to circumscribe regions-of-interest (ROIs) on the images, thereby increasing the speed of analysis. The methodology described here can produce 3D habitat maps of the analyzed organs which can be used for diagnosis, prognostication and evaluation of treatment response.

Figure 29:
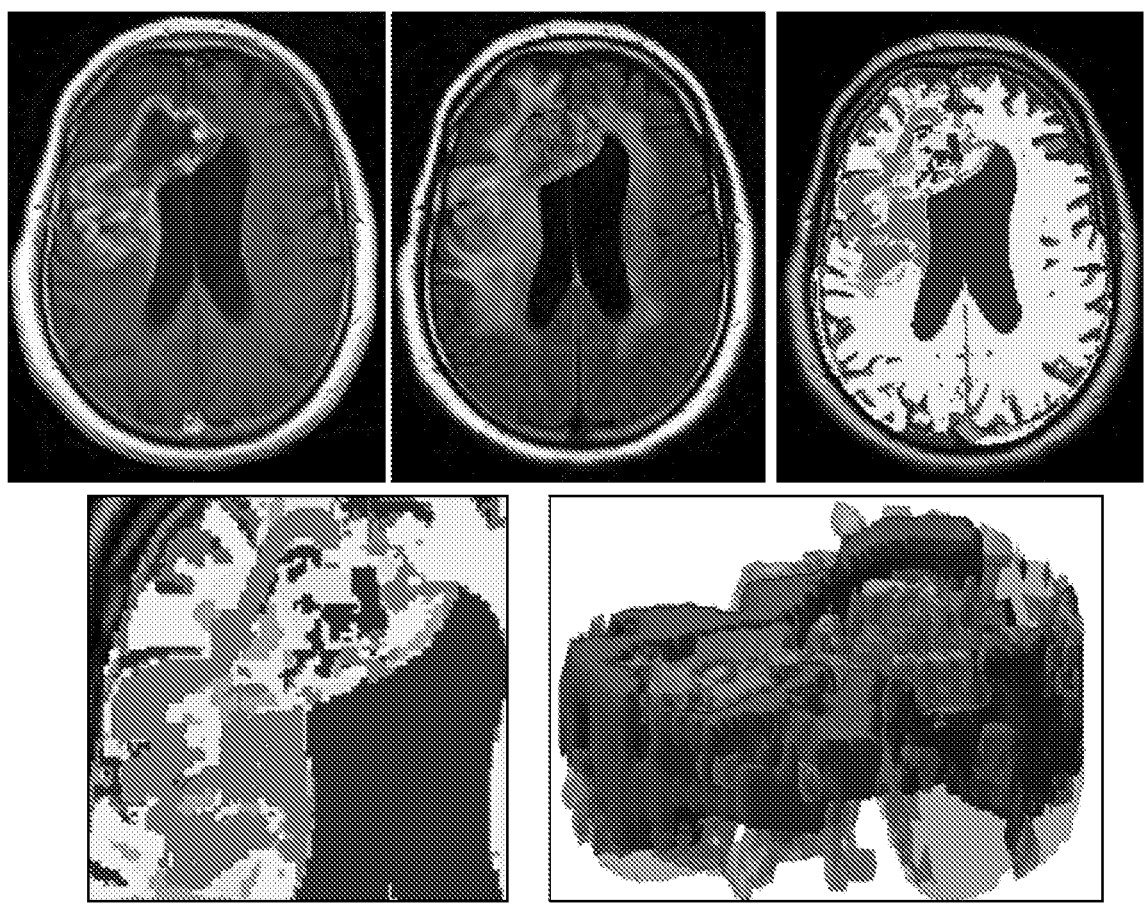
FIG. 29. Whole brain images from T1-weighted post-contrast (top row, left panel) and FLAIR (top row, middle panel) sequences acquired on a patient with a recurrent Glioblastoma multiforme (GBM) tumor. A 3D multi-parametric tumor habitat map was constructed as per the method in FIG. 28 (top row, right panel). A zoomed-in region of the habitats within the tumor is shown in the left panel of the bottom row, with each color representing a distinct "habitat". A 3D rendering of these same habitat maps (bottom row, right panel) illustrates the spatial coherency of the habitats identified by this method.

In one embodiment, routine MRI images such as T1-weighted pre-contrast (with or without fat suppression), T1-weighted post-contrast (with or without fat suppression), T2-weighted pre-contrast, fluid attenuated inversion recovery (FLAIR), and Apparent Diffusion Coefficient of water (ADC) maps are examined Rigid-body and/or elastic image registration can be used to render the images from the different MRI sequences superimposable in 3D prior to performing the analysis. Classification of pixels into clusters at each node in the methodology depicted in FIG. 28 can be based on pixel intensity and this classification may be based on Otsu thresholding [Nobuyuki Otsu (1979). IEEE Trans. Sys., Man., Cyber. 9(1): 62-66] or another suitable method. For this application, a global image thresholding method that segments the image into classes based on the Otsu method was implemented in MATLAB. The histogram-based method determines the thresholds that minimize the weighted within-class variance. Given an array of pixel intensities, the method returns a matching array of cluster indices assigned to each pixel. An example of the use of this method to objectively identify different normal and pathologic tissue in a patient with Glioblastoma multiforme is depicted in FIG. 29. In particular this methodology can identify 3D volumes in the images corresponding to increased immune infiltration into the tumor following response to immunotherapy ("treatment-induced changes" in FIG. 29).

Example 6

Segmenting MRI Images of Renal Cell Carcinoma into 3D Habitat Maps

In another embodiment, superimposable standard-of-care MRI images routinely prescribed in the setting of renal cell carcinoma can be used, e.g., T1-weighted pre-contrast, T1-weighted post-contrast (typically more than one temporal phase), T2-weighted pre-contrast, and ADC maps. Information from superimposable Computed Tomography (CT) images can be incorporated into the decision tree to increase the combined diagnostic power of the method. Rigid-body and/or elastic image registration can be used to render the images from the different MRI sequences and CT superimposable in 3D prior to performing the analysis. Classification of pixels into clusters can be accomplished analogously to the decision tree depicted in FIG. 28. This method can separate tumor pixels into distinct clusters based on the degree of sarcomatoid vs. non-sarcomatoid differentiation, and this information can be used to objectively determine the degree of sarcomatoid differentiation in renal cell carcinoma.

Example 6

Segmenting MRI Images of Soft Tissue Masses into 3D Habitat Maps

In yet another embodiment, superimposable standard-of-care MRI images routinely prescribed in the setting of soft tissue masses of the extremities can be used, e.g., T1-weighted pre-contrast (with or without fat suppression), T1-weighted post-contrast (with or without fat suppression), Short Tau Inversion Recovery (STIR), and ADC maps. Additional sequences, such as T2*-weighted gradient-echo images, if available, can be incorporated into the decision tree to increase the combined diagnostic power of the method. Rigid-body and/or elastic image registration can be used to render the images from the different MRI sequences superimposable in 3D prior to performing the analysis. Classification of pixels into clusters can be accomplished analogously to the decision tree depicted in FIG. 28. This method can separate tumor pixels into distinct clusters representing benign or malignant transformation, and that information can be used for an objective diagnosis.

Unless defined otherwise, all technical and scientific terms used herein have the same meanings as commonly understood by one of skill in the art to which the disclosed invention belongs. Publications cited herein and the materials for which they are cited are specifically incorporated by reference.

Those skilled in the art will recognize, or be able to ascertain using no more than routine experimentation, many equivalents to the specific embodiments of the invention described herein. Such equivalents are intended to be encompassed by the following claims.

What is claimed is:

1. A radiological method for predicting the severity of a tumor in a subject, comprising
    (a) spatially superimposing two or more radiological images obtained by a magnetic resonance imaging (MRI) sequence thereby creating a spatial map of the tumor sufficient to define regional habitat variations in at least perfusion (blood flow) and interstitial cell density (edema) in the tumor, wherein the MRI sequence comprises i) defining perfusion variations using longitudinal relaxation time (T1)-weighted images and ii) defining interstitial cell density (edema) using transverse relaxation time (T2)-weighted images or fluid attenuated inversion recovery (FLAIR); and
    (b) comparing the habitat variations from the spatial map of the tumor in the subject to one or more controls to predict the severity of the tumor.

2. The method of claim 1, wherein the tumor is a glioblastoma multiforme (GBM).

3. The method of claim 1, wherein the tumor is prostate cancer.

4. The method of claim 1, wherein the tumor is a soft tissue sarcoma.

5. The method of claim 1, wherein the tumor is a pancreatic cancer.

6. The method of claim 1, further comprising defining regional habitat variations by extracellular pH (pHe).

7. The method of claim 1, further comprising defining regional habitat variations by hypoxia.

8. The method of claim 1, wherein the MRI sequence further comprises short tau inversion recovery (STIR).

9. The method of claim 1, wherein the regional habitat variations are defined using a fuzzy clustering algorithm analysis of the radiological images.

10. The method of claim 1, wherein the regional habitat variations are defined using a thresholding algorithm analysis of the radiological images.

11. The method of claim 1, wherein the method predicts the survival of the subject based on the severity of the tumor.

12. The method of claim 1, wherein detection of relatively low heterogeneity in regional habitats is an indication of low severity of the tumor.

13. The method of claim 1, wherein detection of relatively high heterogeneity in regional habitats is an indication of high severity of the tumor.

14. The method of claim 1, wherein detection of relatively high cell density and relatively high perfusion in the tumor is an indication of low severity of the tumor.

* * * * *

UNITED STATES PATENT AND TRADEMARK OFFICE
CERTIFICATE OF CORRECTION

PATENT NO. : 10,827,945 B2
APPLICATION NO. : 15/124718
DATED : November 10, 2020
INVENTOR(S) : Robert J. Gillies et al.

Page 1 of 1

It is certified that error appears in the above-identified patent and that said Letters Patent is hereby corrected as shown below:

In the Specification

Column 1, Lines 16-18:
"This invention was made with Government Support under Grant No. CA143970, CA143062, CA077575, CA17059, and CA076292 awarded by the National Institutes of Health."

Should read:
"This invention was made with Government Support under Grant No. CA143970, CA143062, CA077575, CA170595, and CA076292 awarded by the National Institutes of Health."

Signed and Sealed this
Twenty-first Day of December, 2021

Drew Hirshfeld
*Performing the Functions and Duties of the*
*Under Secretary of Commerce for Intellectual Property and*
*Director of the United States Patent and Trademark Office*